United States Patent
Tella et al.

(10) Patent No.: US 12,188,871 B2
(45) Date of Patent: Jan. 7, 2025

(54) RAMAN ANALYSIS OF PHARMACEUTICAL DOSAGE FORMS

(71) Applicant: Agilent Technologies LDA UK Limited, Cheadle (GB)

(72) Inventors: Richard Tella, Sunnyvale, CA (US); Craig Peters, Melbourne (AU)

(73) Assignee: Agilent Technologies LDA UK Limited, Cheadle (GB)

(*) Notice: Subject to any disclaimer, the term of this patent is extended or adjusted under 35 U.S.C. 154(b) by 316 days.

(21) Appl. No.: 17/631,300

(22) PCT Filed: Jul. 22, 2020

(86) PCT No.: PCT/GB2020/051751
§ 371 (c)(1),
(2) Date: Jan. 28, 2022

(87) PCT Pub. No.: WO2021/019208
PCT Pub. Date: Feb. 4, 2021

(65) Prior Publication Data
US 2022/0283091 A1 Sep. 8, 2022

(30) Foreign Application Priority Data
Jul. 29, 2019 (GB) ...................... 1910801

(51) Int. Cl.
*G01N 21/65* (2006.01)
*G01N 33/15* (2006.01)
*G01N 35/00* (2006.01)

(52) U.S. Cl.
CPC ............. *G01N 21/65* (2013.01); *G01N 33/15* (2013.01); *G01N 35/0099* (2013.01)

(58) Field of Classification Search
CPC ........ G01N 21/65; G01N 21/13; G01N 33/15; G01N 33/0099
See application file for complete search history.

(56) References Cited

U.S. PATENT DOCUMENTS

| | | |
|---|---|---|
| 2007/0224683 A1 | 9/2007 | Clarke et al. |
| 2013/0022250 A1 | 1/2013 | Nygaard et al. |
| 2020/0064255 A1 | 2/2020 | Boss |

FOREIGN PATENT DOCUMENTS

| | | |
|---|---|---|
| EP | 3367103 A1 | 8/2018 |
| JP | S60104752 U | 7/1985 |

(Continued)

OTHER PUBLICATIONS

Haichen Nie, "Analytical approaches to investigate salt disproportionation in tablet matrices by Raman spectroscopy and Raman mapping", 2015 (Year: 2015).*

(Continued)

*Primary Examiner* — Maurice C Smith

(57) ABSTRACT

There are disclosed methods and apparatus for automatic analysis of pharmaceutical dosage forms. In some aspects a dosage form may be grasped by a gripper which is used to bring the dosage form to a test location and to present the dosage form in a plurality of different alignments between delivery and collection optics. Probe light scattered through the dosage form is collected during each alignment. The collected probe light for the plurality of alignments is then used for Raman spectral analysis of the dosage form. In other aspects a rotation stage is used to rotate a dosage form on the stage to a preferred alignment before being grasped by a gripper. The gripper is then used to carry the dosage form to the test location for optical analysis.

18 Claims, 11 Drawing Sheets

(56) References Cited

FOREIGN PATENT DOCUMENTS

| | | | | |
|---|---|---|---|---|
| JP | H10160554 A | | 6/1998 | |
| JP | 2009536317 A | * | 8/2009 | ............. G01N 33/22 |
| JP | 2018516356 A | | 6/2018 | |
| WO | 2004069409 A2 | | 8/2004 | |
| WO | 2013072710 A1 | | 5/2013 | |
| WO | WO-2018158661 A1 | * | 9/2018 | ............. G01N 21/03 |

OTHER PUBLICATIONS

"International Search Report and Written Opinion mailed on Nov. 24, 2020," Application No. PCT/GB2020/051751, 11 pages.
UKIPO "Search Report mailed on Jan. 28, 2020," Application No. 1910801.8, 5 pages.
UKIPO "Search Report mailed on Jun. 17, 2020," Application No. 1910801.8, 12 pages.
EPO, et al., "Extended European Search Report mailed on Jun. 26, 2023," Application No. 23175587.7, 8 pages.

* cited by examiner

RAMAN ANALYSIS OF PHARMACEUTICAL DOSAGE FORMS

CROSS-REFERENCE TO RELATED APPLICATIONS

This application is a US national stage entry of PCT/GB2020/051751, filed Jul. 22, 2020, which claims priority to GB Application No. 1910801.8, filed Jul. 29 2019.

The present invention relates to apparatus and methods for carrying out Raman or other optical or spectroscopic analysis of pharmaceutical dosage forms, including oral solid dosage forms such as tablets or capsules. For example, such dosage forms may be analysed using Raman spectroscopy in a transmission configuration.

INTRODUCTION

In various situations such as production line sampling it is desirable or necessary to test pharmaceutical dosage forms to check compliance with particular specifications. Such specifications may define narrow acceptable ranges of absolute content of one or more active pharmaceutical ingredients (APIs), as well as other aspects such as shape, size, and content of other chemical components and properties of the dosage form.

One way of determining such content and chemical properties is to separately grind each sample dosage form to a powder, dissolve in a solvent, and introduce to a liquid chromatograph, mass spectrometer or similar device. However, when large numbers of dosage forms need to be individually tested this process can be slow and difficult to automate effectively. Difficulties of accurately tracking the identity of each dosage form sample through such an analysis process arise, and physical properties and identifying markings of the original dosage form are lost in the process.

Spectroscopic testing of pharmaceutical dosage forms for quantitative analysis is described for example in PCT/SE96/01637, and WO2007/113566. Dosage forms may take the form of tablets, capsules and other formulations.

The invention seeks to address problems and limitations of the related prior art.

SUMMARY OF THE INVENTION

Aspects of the invention provide apparatus and methods for automatically handling and presenting dosage form samples for optical analysis with minimal or zero operator input, and can be arranged to handle many different sizes and shapes of dosage form, and to switch between different sample or dosage form types without user input, for example to automatically process dosage forms of different types stored in different hoppers without user intervention. Dosage forms can be tracked and managed through the handling and analysis process with minimal or zero scope for handling errors or mistaken sample loading. Physical dimensions and markings of a dosage form can be determined and checked against expected values and patterns.

Aspects of the invention also enable individual dosage forms to be weighed accurately. Since optical analysis such as transmission configuration Raman techniques typically provide proportional content measurements such as percentage content of an active pharmaceutical ingredient (% API), having the dosage's weight enables a more accurate absolute measure of API dosage to be determined for the sample under test.

Aspects of the invention also enable individual dosage forms to be manipulated flexibly so that inconsistencies in results of optical analysis can be avoided by improved consistency of presentation of samples during optical analysis.

Each pharmaceutical dosage form may be a tablet, a coated tablet, a capsule, a gelcap, or any of a variety of other forms. Such dosage forms may be described as solid dosage forms, which can be individually manipulated by a mechanical gripper or the like, although some such solid dosage forms may contain liquids or gels within them. Such dosage forms may also be described as oral dosage forms, which are intended to be taken by swallowing.

Dosage forms to be processed by the methods and apparatus may display one or more of surface markings, debossing (e.g. features pressed into the dosage form during manufacture), embossing (features standing proud of the dosage form), a plurality of surface regions each having a different colours, printed markings, and so forth. The presence of such features can affect the results of optical, and in particular spectral analysis of such dosage forms, so that to achieve consistency of quantitative analysis of the dosage forms, consistency in presentation for optical interrogation is found desirable.

In particular, aspects of the invention provide an apparatus for analysing a pharmaceutical dosage form, the apparatus comprising: a dosage handler arranged to bring a dosage form into a predetermined and preferred rotational state or orientation (such as alignment of a defined axis of the dosage form into a preferred direction and/or orientation of the dosage form about that axis) in response to detection of the dosage form by a machine vision system; and an optical analysis station for testing the dosage form. Various arrangements can be provided for ensuring that the dosage form remains in a preferred rotational state or orientation when presented to the optical analysis station for testing, although known rotations or other changes in alignment may occur in moving the dosage form to and then within the optical analysis station as required.

The dosage handler may for example comprise a rotation stage or turntable arranged to rotate a dosage form lying on the stage, with the rotation being controlled responsive to data received from the machine vision system. The rotation stage may provide a substantially level or flat, and typically circular, upper surface on which the dosage form lies, and may therefore be used to rotate the dosage form about a vertical axis. The dosage handler may also or instead comprise a mechanical gripper or other manipulator arranged to carry out one or more of: rotation of the dosage form responsive to the machine vision system, for example about an axis oblique or perpendicular to an axis of rotation of the rotation stage, so typically about a horizontal axis; and carrying the dosage form to the optical analysis station for testing. The dosage handler may also comprise a weighing scale arranged to weigh a dosage form lying on the weighing scale, typically in advance of rotation and/or manipulation as mentioned above. Such a weighing scale may be provided adjacent to the rotation stage, for example by both the rotation stage and weighing scale being provided in the surface of a handling table.

The optical analysis station may typically be arranged to carry out Raman spectral interrogation of a dosage form, for example in a transmission configuration, and this may be carried out while still being held by the mechanical gripper or other manipulator following collection from the rotation stage or other parts of the dosage handler.

Other aspects of the invention provide apparatus for analysing a pharmaceutical dosage form, comprising: a rotation stage having a rotation stage surface arranged to receive a dosage form; a gripper or manipulator arranged to grasp the dosage form; an optical analysis station having a test location and arranged to detect spectral features in probe light scattered within the dosage form when positioned at the test location; and a controller arranged to control rotation of the rotation stage so as to rotate the dosage form when on the stage surface to a preferred alignment, orientation or state of rotation, to control the gripper to grasp the dosage form in the preferred alignment, orientation or state of rotation, and to control the gripper to carry the grasped dosage form to the test location for spectral interrogation and analysis.

This enables each dosage form to be presented at the optical analysis station with a consistent and preferred alignment, orientation, or state of rotation, to thereby reduce presentation bias which can otherwise lead to marked variations in results of the optical analysis, especially when dosage forms have marked asymmetries or markings such as coloured areas, debossing, and so forth. The rotation stage surface may be in the form of a substantially flat and level surface, which may typically be circular, on which the dosage form rests so as to be located above the surface.

The optical analysis station may in particular be a Raman analysis station arranged to detect Raman spectral features of the tested dosage form The Raman analysis station may comprise: delivery optics arranged to direct probe light to a first surface region of the dosage form when located at the test location; collection optics arranged to receive said scattered probe light from a second surface region of the dosage form, the second surface region being spaced from the first surface region; and a detector arranged to detect the Raman spectral features in the received probe light. The Raman analysis station can thereby interrogate a dosage form using a transmission geometry, to obtain spectral measurements representative of a bulk of the dosage form, for example as described in WO2007/113566.

The second surface region may be on an opposite side of the dosage form from the first surface region to help maximise the volume of the dosage form which is represented by results of the spectral analysis.

The apparatus may be arranged such that the gripper holds the dosage form at the test location for Raman analysis in free space, for example without other structures such as a carrier, or optical baffles between the delivery optics and the collection optics provided as part of the Raman analysis station. Moreover, because of the Raman techniques used for analysis in which the spectral features for detection are spectrally distanced from the fundamental laser frequency, the gripper need not be provided with any light blocking baffles for example in the form of elastically yielding material or a more rigid holder or mount.

More particularly, it is not necessary to provide a holder or mount which provides a close fit around the dosage form at the test location in order to block laser light from scattering around or passing the dosage form. Nor is it necessary for the dosage form to rest or be placed in any such close fitting holder or mount, although such a holder or mount may none-the-less be provided if desired.

The apparatus may further comprise an analyser arranged to determine one or more properties of the dosage form from the detected Raman spectral features, such as percentage content of an active pharmaceutical ingredient (API), proportional content of other chemical components, and so forth. Such proportional measures may be used to determine absolute content measures for example an amount of an API, by combining with a determined weight of a dosage form which can be found using a weighing scale of the apparatus as discussed below.

The apparatus may further comprise a machine vision system arranged to detect alignment of the dosage form when on the rotation stage surface, and to pass the detected alignment of the dosage form to the controller for controlling rotation of the rotation stage to rotate the dosage form to the preferred alignment. For example, the machine vision system may be arranged to detect alignment or orientation of a predefined dosage axis of the dosage form, and the preferred alignment or orientation comprises a preferred alignment or orientation of the dosage axis. To this end the machine vision system may be provided in advance with geometric and optionally also surface marking details of the dosage form to be manipulated, and these details may include explicitly or implicitly such a predefined dosage axis.

The gripper or manipulator may be arranged to rotate a grasped dosage form about a gripper rotation axis, and the controller is then arranged to control the gripper while grasping the dosage form so as to rotate the dosage form into a preferred orientation of rotation about the gripper rotation axis. If the dosage form has already been rotated into the preferred alignment by the rotation stage then the gripper rotation axis may be parallel to the preferred alignment of the dosage axis. Typically, the gripper rotation axis may be parallel to the rotation stage surface and therefore also typically perpendicular to an axis of rotation of the rotation stage. This rotation by the gripper is typically also carried out using data from the machine vision system. To this end, the machine vision system may also be arranged to detect the orientation of rotation of the dosage form about the gripper rotation axis, and to pass the detected orientation of rotation to the controller for controlling the gripper in rotating the dosage form into the preferred orientation of rotation.

The machine vision system may also be arranged to detect a lateral position of the dosage form on the rotation stage surface, and to pass the detected lateral position to the controller for controlling the gripper to grasp the dosage form in the detected lateral position.

The machine vision system may be further arranged to determine one or more dimensions of the dosage form, such as length, width, diameter or other dimensions of the dosage form in plan view when lying on the rotation stage. If the dosage form has opposing major faces separated by an edge face, then in order to determine a thickness of the dosage form between the opposing major faces the controller may be arranged to control the gripper to rotate the dosage form to present an edge of the dosage form, instead of a major face, in plan view to the machine vision system, and the machine vision system is then arranged to determine a thickness of the dosage form from the plan view of the presented edge.

In some examples, detection of the edge face by the machine vision system may be achieved while the dosage form is being held by the gripper. However, in other examples the controller may be arranged to control the gripper to place the dosage form on edge onto the rotation stage, and to release the dosage form in that position, for determination of a thickness of the dosage form by the machine vision system. This may be useful for example when the gripper would otherwise obscure a view of the edge for the machine vision system.

Using the gripper to present a dosage form in edge orientation to the machine vision system may particularly be used when the machine vision system uses one or more downward facing cameras looking down at the rotation stage, but is not provided with any cameras looking sideways across the rotation stage which might in principle detect a dosage form thickness, but which would add expense and complexity to the system.

Although different types of manipulator or gripper may be used, the gripper may comprise opposing jaws arranged to grasp a dosage form between the jaws. The opposing jaws may be arranged to grasp the dosage form by closing on the dosage form along at least one of: an axis parallel to the rotation stage surface; and along the gripper rotation axis. In particular, the direction of the gripper rotation axis may be fixed, thereby simplifying the construction of the apparatus, while the gripper will typically be provided with three translational axis of movement.

The gripper may be arranged such that the dosage form remains in the preferred alignment when held at the test location for Raman analysis. Note that the direction of the preferred alignment as achieved using the rotation stage may transform to a different direction when held at the test location, as long as that transformation is known and accurately controllable.

Each jaw of the gripper may comprise a concave surface presented to the dosage form for grasping the dosage form when the jaws close on the dosage form.

The controller may be arranged to control the gripper or manipulator to deposit the dosage form in a predetermined cell of an output tray or other output structure or arrangement, following detection of Raman spectral features in probe light scattered within the dosage form when positioned at the test location.

The apparatus may comprise a handling table for use in manipulating and other testing of each dosage form. For example, the rotation stage surface may form part of a table surface of the handling table. The apparatus may comprise a weighing scale having a weighing scale surface forming part of the table surface, and arranged to weigh a dosage form when positioned on the weighing scale surface. The weight of the dosage form can be combined with results from the spectral analysis to determine and output one or more absolute measures of content of the dosage form, for example a measure of a weight or other absolute amount of an API.

The apparatus may further comprise a dosage form source, the dosage form source being arranged to deposit a dosage form in a drop zone of the table surface. To avoid temporary reduction in accuracy of the weighing scale, the drop zone may typically be separate from the weighing scale, and optionally separate from the rotation stage surface. The dosage form source may comprise a plurality of hoppers, the apparatus being arranged to select a dosage form from a particular hopper for analysis. In this way, different types or specifications of dosage forms may be loaded into each hopper by a user, and then the apparatus may automatically carry out the required handling and optical analysis of dosage forms of a plurality of different types without further user intervention.

The apparatus may further comprise a slider arranged to slide a dosage form across the table surface under control of the controller. For example, the controller may be arranged to control the slider to slide the dosage form from the drop zone to the weighing scale surface for weighing, and from the weighing scale surface to the rotation stage surface for alignment and any other required orientation.

The slider may be a box slider arranged to surround a dosage form for sliding across the table surface. Providing slider walls surrounding the dosage form, for example in a rectangular or square configuration, loss of the dosage form from control by the apparatus can be avoided for example when a dosage form is dropped from the dosage source onto the table surface. The slider will typically be provided with three axes of translational movement, including a vertical axis enabling the slider to rise above the level of the dosage form so that the slider can be moved away leaving the dosage form unmoved on the table surface.

The gripper and the slider may both be coupled to a multi-axis staging providing common motion to both the gripper and the slider. For example, the multi-axis staging may provide motion along a process axis under control of the controller, to thereby move the slider between the drop zone, the weighing scale surface, and the rotation stage surface, and to move the gripper between the rotation stage surface and the test location of the Raman analysis station.

The invention also provides methods such as methods of handling, manipulating, testing, optical interrogation, analysis, and quantitative analysis of dosage forms, including methods of controlling aspects of apparatus described herein.

According to one aspect, the invention provides a method of automatically analysing a pharmaceutical dosage form, comprising: receiving the dosage form on a rotation stage; rotating the rotation stage so as to rotate the dosage form about a rotation stage axis into a preferred alignment or orientation; carrying the dosage form from the rotation stage to a test location of an spectral analysis station; and performing optical interrogation of the dosage form at the test location.

The optical interrogation may comprise spectral interrogation of the dosage form, for example to detect one or more Raman spectral features of light scattered with the dosage form, and the method may further comprise determining one or more properties of the dosage form from results of the spectral interrogation, such as quantitative properties of chemical components.

Performing spectral interrogation may comprise using a transmission geometry, for example directing laser probe light to a first surface region of the dosage form, collecting elements of the laser probe light scattered within the dosage form from a second surface region of the dosage form, the second surface region being on an opposite side of the dosage form from the first surface region, and detecting Raman spectral features in the collected light.

The carrying may be carried out by using a gripper or other manipulator to grasp the dosage form when in the preferred alignment or orientation, using the gripper to carry the grasped dosage form to the test location, performing spectral interrogation of the grasped dosage form, and only subsequently to this releasing the dosage form from the grasp of the gripper.

The gripper may also be used to rotate the dosage form about a gripper rotation axis to a preferred orientation about that axis, to thereby further reduce presentation bias of the dosage form during optical interrogation. Rotation of the dosage form about the gripper rotation axis may typically be carried out after rotation of the dosage form about the rotation stage axis using the rotation stage, so that the dosage form is already in a desirable alignment for grasping by the gripper, but more than one step of rotation using the rotation stage may be used for example both before and after rotation by the gripper.

The method may further comprise: receiving the dosage form at a drop zone of a handling table, the handling table also comprising a weighing scale and the rotation stage; sliding the dosage form across the handling table from the drop zone to the weighing scale; weighing the dosage form using the weighing scale; and sliding the dosage form across the handling table from the weighing scale to the rotation stage to be rotated to the preferred alignment or orientation, and to be subsequently carried to the test location.

Methods are also provided for determining aspects such as variance in the handling and optical interrogation of dosage forms, for example by repeating the above steps either on a single dosage form or on a plurality of dosage forms of the same type, so as to carry out a plurality of said optical interrogations; and comparing results of the plurality of optical interrogations to determine at least one measure of variance in the handling and optical interrogation of the dosage forms.

Methods of automatically analysing a plurality of pharmaceutical dosage forms may also comprise: loading a plurality of dosage forms of each of a plurality of dosage form types, the dosage forms of each type being loaded in a separate hopper; and carrying out the described manipulation and optical analysis for each dosage form, wherein receiving a particular dosage form on the rotation stage or other part of the dosage handler comprises receiving the dosage form from the hopper in which it has been loaded.

The invention also provides method and apparatus for improved optical testing of a dosage form, for example during presentation by a gripper or other handling element at a Raman analysis station or other test location. By adjusting the alignment of the dosage form so as to determine Raman spectral features for a range of such alignments, including translations and/or rotations of the dosage form, improved sampling of the dosage form can be achieved. This may involve detecting Raman spectral features for a range of such alignments so as to determine a property of the dosage formulation which is more representative of the dosage formulation as a whole, and/or may involve determining a value for a property for different parts of the same dosage formulation such as breakable sub doses of a tablet.

Multiple such alignments can be achieved more readily using the described arrangements because of the use of Raman spectroscopy which permits the dosage form to be held at the test location without light baffles or other arrangements to strongly prevent probe light from passing around the dosage form to the probe light collection optics. This is in contrast to the use of infrared absorption spectroscopy where leakage of probe light around the dosage form is of much more concern, so that optical testing of the dosage form over a range of alignments (translations and/or rotations) is much more difficult.

To this end, the invention provides a method of automatic analysis of a pharmaceutical dosage form, comprising: grasping the dosage form using a gripper; moving the gripper so as to bring the dosage form to a test location between delivery optics arranged to direct probe light to a first surface region of the dosage form, and collection optics arranged to receive probe from a second surface region of the dosage form following scattering through said dosage form; moving the gripper to present the dosage form in a plurality of alignments between the delivery optics and the collection optics, and for each alignment, collecting probe light from said second surface; and detecting Raman spectral features of received probe light for each of the plurality of alignments.

One or more properties of the dosage form, such as a relative concentration of an active pharmaceutical ingredient, may then be determined using the Raman spectral features detected during some or all of the alignments. Raman spectral features from all of the alignments can be used for example to determine an improved average property of the dosage formulation as a whole. In other embodiments, however, a different value of a particular property may be determined for each of two or more parts of the dosage form, using one or more alignments corresponding to each such part of the dosage form. This technique may be useful for determining the value of a property for each of multiple frangible parts of a dosage form, in which two or more parts of a tablet may typically be defined by break lines provided on a surface of the tablet.

The multiple alignments of the dosage form may be understood as providing a change in at least one of the position of the first surface region on the dosage form and the position of the second surface region on the dosage form, between each alignment. To this end, between each alignment the gripper may move the dosage form through one or both of a translation and a rotation. However, note that one or both of discrete alignments and continuous movement through one or more ranges of alignment may be used. To this end, at least some of the alignments may form one or more continuous ranges of alignments during movement of the dosage form and in which the Raman spectral features are detected in the received probe light.

The optical testing may use a transmission arrangement, in which the second surface region is on an opposite side of the dosage form from the first surface region. As noted elsewhere, the pharmaceutical dosage form may be one or more of: a tablet; a coated tablet; a capsule; a gelcap; a solid dosage form; and an oral dosage form. The range of movement of a dosage form in providing the plurality of alignments may include at least one of: translation of the dosage form over a distance of at least 2 mm; and rotation of the dosage form through at least 10 degrees.

The invention provides corresponding apparatus for providing optical testing of a dosage form using a plurality of alignments, such as apparatus for automatic analysis of a pharmaceutical dosage form, comprising: a mechanical gripper arranged to grasp the dosage form; a Raman analysis station having a test location and arranged to detect Raman spectral features in probe light scattered within the dosage form when positioned at the test location; a controller arranged to control the gripper so as to present the dosage form in a plurality of alignments within the test location, and to control the Raman analysis station to collect probe light scattered within the dosage form and detect Raman spectral features in the collected probe light, in each of the alignments; and an analyser arranged to determine one or more properties of the dosage form from the detected Raman spectral features.

The invention also provides a controller and/or one or more other computer systems comprising computer program code arranged to carry out method steps as described herein, as well as providing such computer program code, and a one or more computer readable media carrying such computer program code.

BRIEF SUMMARY OF THE DRAWINGS

Embodiments of the invention will now be described, by way of example only, and with reference to the drawings of which.

DETAILED DESCRIPTION OF PREFERRED EMBODIMENTS

Figure 1:
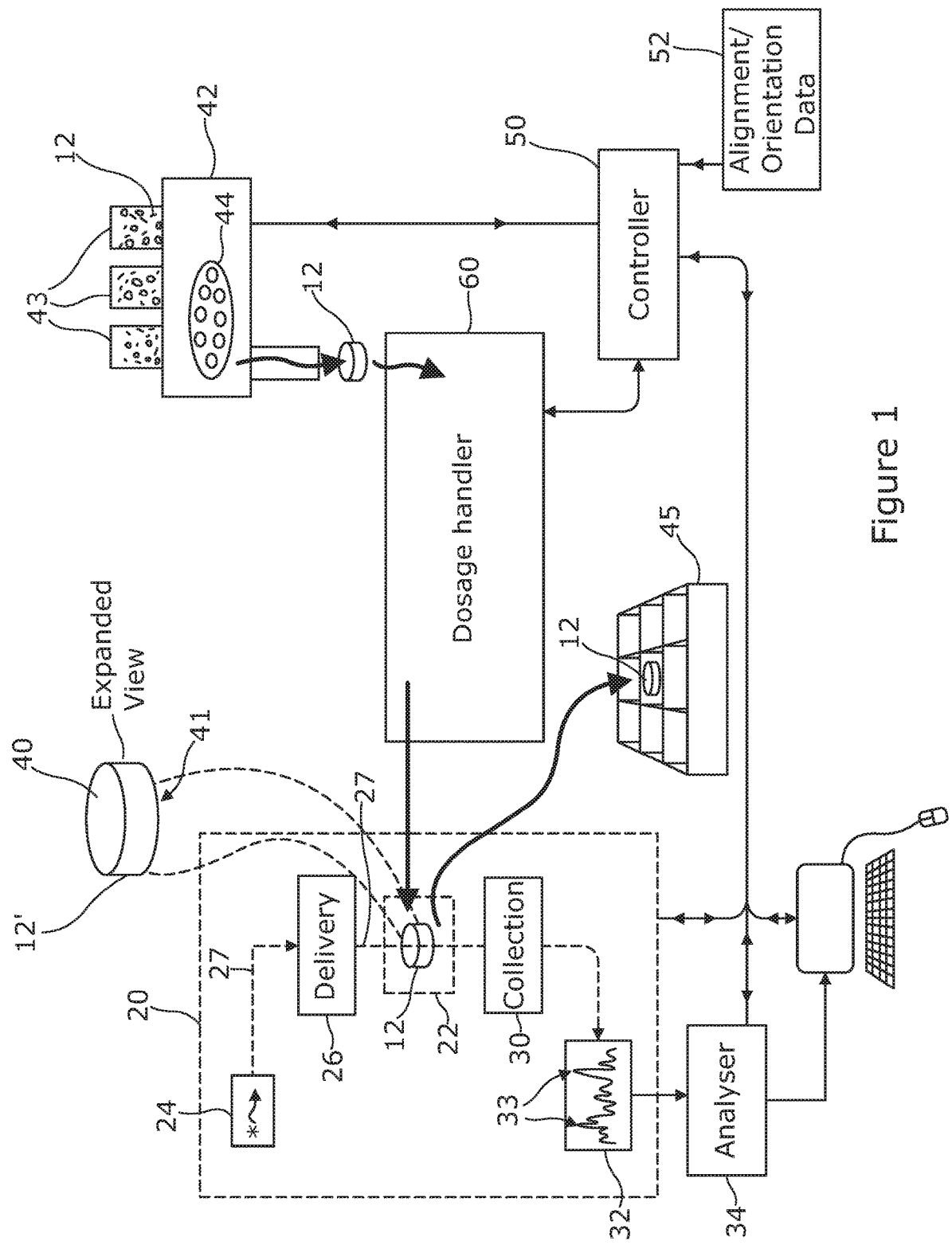
FIG. 1 shows schematically apparatus for handling and optical interrogation and analysis of a plurality of pharmaceutical dosage forms.

Referring to FIG. 1, there is shown schematically apparatus 10 for spectral or other optical analysis of pharmaceutical dosage forms 12, and in particular of oral solid dosage forms such as tablets or capsules, although other types of dosage forms or indeed other kinds of objects altogether may be analysed using the apparatus.

The apparatus 10 is arranged and operated to provide improved consistency of spectral or other optical analysis across a batch of such dosage forms which are intended to be substantially identical. Dosage forms of a batch may typically be superficially identical or very similar, for example in terms of shape, size and composition, but may still comprise defects and/or variations especially in internal chemical content and composition. It may be important to detect such defects and variations as part of a manufacturing process or other test scenario.

Pharmaceutical tablets are manufactured in a variety of shapes, sizes and colours. Some tablets may be of multiple different colours. Tablet shapes include cylindrical or elliptical prism forms, often with bevelled edges, spherical, ovoid, lozenge forms and so forth. Tablets are frequently embossed or debossed with markings such as alphanumeric codes and other symbols, slots to assist breaking into parts, and other surface features. Some tablets carry printed surface markings, for example including alphanumeric codes and other symbols. Tablets are manufactured both in coated forms in which a surface layer comprises different components to an underlying tablet core, and in uncoated forms.

Pharmaceutical capsules, of which gel capsules are one particular form, typically comprise an encapsulating sleeve containing pharmaceutical powders or sometimes gels or fluids. A typical shape for a capsule is cylindrical with rounded ends, but other geometries are sometimes used, for example flattened cylindrical forms. The encapsulating sleeve is typically formed by joining two opposing end sections, which are frequently of different colours. Capsules are often printed with surface markings such as alphanumeric codes and other symbols.

The inventors have found that various physical features of dosage forms such as those mentioned above can affect the consistency of results of optical analysis between a number of such dosage forms of the same type or batch even if these are superficially identical. It has been determined that consistency may be reduced for example if such dosage forms are presented for optical analysis in different orientations or rotational states of those features with respect to the optical analysis equipment. Very few dosage forms which it might be desirable to analyse optically are essentially devoid of any such features or asymmetries, although some dosage forms may be sufficiently symmetric about one axis of rotational symmetry such that rotation of the dosage form about that axis is difficult to detect at least visually for example by a machine vision system, in which case rotation about this axis does not contribute in any effective way to consideration of rotational state of the dosage form during handling for subsequent optical analysis.

The apparatus as illustrated in FIG. 1 can be used to provide for automatic and sequential optical analysis of a plurality of such superficially identical or similar dosage forms, with improved consistency of optical analysis.

Typical application areas may be for monitoring chemical composition of dosage forms sampled from a production line or other manufacturing process. Determined properties of the dosage forms may include measurements or concentrations or quantities of one or more active ingredients or other components, as well as measurements or concentrations or quantities of polymorph forms, hydrated forms, solvate forms, salt forms, and degrees of crystallinity of one or more such active ingredients or components. The presence or concentration of impurities may similarly be detected.

The apparatus illustrated in FIG. 1 is particularly arranged to carry out Raman spectral analysis of dosage forms 12, although other types of spectral or more generally optical analysis could also or instead be implemented. To this end the apparatus comprises a Raman analysis station 20 which is arranged to detect Raman spectral features 33 in probe light scattered within a dosage form 12 when positioned in a test location 22 of the station.

The Raman analysis station 20 of FIG. 1 comprises a laser source 24 arranged to generate a laser beam of probe light, typically of infrared light, delivery optics 26 arranged to direct the probe light to a dosage form 12 in the test location 22, collection optics 30 arranged to receive probe light following scattering, including Raman scattering, within the dosage form 12, and a detector 32 arranged to detect Raman spectral features 33 of the dosage form present in the scattered probe light.

Typically, the laser source 24 may operate in the near infrared, for example around 700 to 1000 nm, either as a continuous wave or pulsed source. Suitable average optical output power delivered to the dosage form 12 may be around 50 to 1200 mW, and a suitable spot diameter of the probe light beam at the dosage form 12 may be in the region of around 1 to 10 mm. Particularly small spot sizes may be avoided due to risks of heat damage to the dosage form under test.

When implementing Raman spectral techniques, the collection optics 30 and/or detector 32 are usually designed to incorporate very good suppression of the wavelength band (i.e. fundamental wavelength) of the probe light as emitted by the laser source 24. Raman scattering cross sections are very small, so without such suppression the fundamental wavelength is likely to adversely affect accurate detection of the Raman spectral features, even though these may be spaced by tens of nanometers or more in wavelength from the laser wave band. This suppression may be achieved using one or more optical filters such as holographic notch filters in the collection optics 30 to suppress the laser waveband light which has been elastically scattered through or around the pharmaceutical solid dosage form to be tested.

Suppression of the laser waveband light in the collection optics 30 when detecting Raman spectral features 33 reduces the need to avoid stray probe light reflecting or scattering around the dosage form 12 and into the collection optics, as would usually be necessary if using infrared absorption spectroscopy and some other spectroscopic techniques. As a result, the dosage form to be tested can be suspended at the test location 22 without particular need for a carrier or other structure providing an optical seal around the sides of the dosage form between the delivery optics 26 and collection optics 30 to prevent such stray light. The dosage form can therefore be suspended between the deliver and collection optics without requiring to be seated within any holder or carrier.

The dosage form 12 may therefore be held in the test location 22 in a "free space" configuration without need for particular optical barriers or optical sealing around the dosage form. In turn, this enables some increased design flexibility in how the dosage form is carried to, held in, and removed from the test location 22, for example using a mechanical gripper to hold the dosage form through all of these steps, as discussed in more detail below. Similarly, the mechanical gripper discussed below need not be provided with any light blocking baffles for example in the form of elastically yielding material.

A dosage form 12 may be presented in the test location 22 at a particular fixed position and state of rotation (orientation/alignment) for the duration of optical testing, or may be moved/rotated between a number of discrete positions with optical testing taking place at each discrete position, and/or may be moved (including either or both of translational movement and rotation) with optical testing taking place during the course of that movement, such as in a scanning action. Such movements may be implemented using the dosage handler described in more detail below, for example by movement of the dosage form within the test location using a gripper 90. However, this geometry of the optical analysis may instead or additionally be varied between discrete testing geometries and/or by scanning using by movement or adjustment of delivery optics 26 and/or collection optics 30 of the Raman analysis station used to deliver probe light to the dosage form and to collect scattered light from the dosage form, or a combination of these aspects.

Multiple optical measurements obtained in such ways during the presentation of a particular dosage form may be combined for example to obtain a more representative optical measurement of the dosage form. For example, by testing a particular dosage form with a laser spot directed at multiple different locations and/or scanned across a range of locations, the optical measurements may better represent the entire bulk of a dosage form. Such techniques may also permit a smaller and/or more consistent laser spot size on the dosage form to be used.

The detector 32 may be implemented in various ways, for example as a spectrometer covering a suitable waveband to detect the desired Raman spectral features 33, for example a Kaiser Optical Technologies Holospec device. Coupling of laser light from the laser source 24 to the delivery optics 26, and between the collection optics 30 and the detector 32 may typically be achieved using optical fibres, although free space transmission arrangements could be used as well or instead.

Spectral data describing at least aspects of the detected Raman spectral features 33 may be passed from the detector 32 to an analyser 34 which is arranged to determine properties of the dosage form from the spectral data, such as the various chemical properties mentioned above. The spectral data may typically take the form of a readout from a CCD or other imaging component of the detector 32, and the analyser 34 may then be arranged to detect aspects such as the magnitudes of particular Raman spectral peaks and other features which represent particular chemical components expected or looked for in the dosage form under test, broader spectral matches to spectra or multiple spectral features of such components, and so forth, for example with reference to one or more data libraries defining expected spectra and/or particular spectral features of such components.

Spectral data and/or determined properties of the tested dosage form may be used in various ways, for example being stored locally and/or remotely, transmitted across a network, further analysed, used to control a process such as a manufacture process used to create the dosage form under test, and so forth. In FIG. 1 a local personal computer 36 is shown as receiving the determined properties, and may for example provide output of aspects of the determined properties to a person monitoring the apparatus 10, for example in the form of displays of deviations of determined properties from expected values, audible or visible alerts to bring the attention of such a person to sufficiently significant deviations, and so forth.

Typically, the probe light may be directed by the delivery optics 26 to a first surface 40 of a dosage form 12 located in the test location 22, and probe light scattered within the dosage form may then be collected from a second surface 41 spaced from the first surface. In this way, the collected probe light will have been scattered at depth within the dosage form 12 under test, and detected Raman spectral features 33 will be representative of bulk properties of the dosage form.

Generally, the second surface 41 may be spaced from the first surface 40 in such a manner that forward scattering of Raman scattered elements of the probe light are transmitted to the second surface to be collected and detected, so that the dosage form is analysed in a transmission or forward scattering geometry. Although different arrangements are possible, typically the second surface 41 may be on an opposite side of the dosage form to the first surface 40. An example of this is illustrated for a tablet dosage form 12' shown in expanded view in FIG. 1, in which the first surface 40 is a first flat surface of the tablet dosage form 12', and the second surface 41 is a second flat surface of the tablet dosage form 12' which is opposite the first surface 40. For some dosage forms and more commonly for tablet forms, each of the first and second surfaces may be substantially parallel, often circular, and spaced from each other by a sidewall.

Some ways in which the Raman analysis station 20 may be arranged and operated to implement analysis using such transmission or forward scattering geometries are described in WO2007/113566, the contents of which are incorporated herein by reference for all purposes.

In some other arrangements, the Raman analysis station 20 may also or instead be arranged to carry out Raman spectral measurements of the dosage form 12 in other geometries and modes, for example using a spatially offset Raman spectroscopy (SORS) mode of operation. In such a mode, probe light is delivered by the delivery optics 26 to one or more entry surface regions of the dosage form 12, and the collection optics 30 are used to collect scattered probe light from one or more collection surface regions that are laterally spaced from the entry region(s). Raman spectral features 13 are then detected in the collected light by detector 32.

The depth profile of the Raman scattering which gives rise to the Raman spectral features 13 in the collected light is then dependent on the lateral spacing. A single spacing between entry and collection surface regions can be used, or Raman spectral features from multiple spacings can be combined to provide more detailed depth dependent measurements, for example a profile of Raman scattering and consequent spectral features as a function of depth within the dosage form. This technique and various implementation details are discussed for example in WO2006/061565 and GB2541110, the contents of which are incorporated herein in their entirety for all purposes.

The Raman analysis station 10 may as well or instead be arranged to implement Raman analysis of a dosage form using other geometries, arrangements or techniques, and in some embodiments other spectral techniques such as ultraviolet, visible, or infrared absorption or reflection spectral techniques, fluorescence techniques, and so forth may be used as well or instead or Raman spectroscopy. In some such modes of optical analysis, delivery and collection optics may be separate or combined or be provided in other more complex forms, with backscatter, transmission or of other types of geometries being used.

As already mentioned above, various asymmetries and features of a dosage form under test, such as overall shape, surface, colour features, debossing and embossing, and printed markings, can affect the results of optical analysis, and very few dosage forms which it might be desirable to analyse optically are essentially devoid of any such asymmetries and features.

When carrying out optical analysis of a dosage form 12, for example using the Raman analysis station 20 described above implementing a transmission geometry, variations in the orientation as well as the position of the dosage form within the test location 22 are found to give rise to variations and errors in the detected Raman spectral features 33 and therefore also in the detected properties of the dosage form under test. Variations in orientation of the dosage form under test can give rise not only to overall changes in intensity of the collected light, but also variations in the relative strengths and apparent wavelengths of various spectral features, for example due to interactions with geometries and properties of the delivery optics, collection optics, and the detector. Different orientations of the dosage form can also give rise to different distributions of both elastic and Raman scattering within the volume of the dosage form.

To achieve more consistent results of optical analysis between similar or essentially identical dosage forms it has been found beneficial to present each such dosage form for optical analysis in the same orientation. Some particular example situations are:
 if a batch of dosage forms comprises tablets with a particular debossing or printing or other markings on one flat face, then those markings should be consistently oriented for testing, for example always facing upwards, or always facing downwards, and always rotated in the horizontal plane to the same orientation;
 if a batch of dosage forms comprises capsules each with two ends of different colours, those ends should be consistently oriented in the same way; and
 if a batch of dosage forms comprises capsules with printing along a cylindrical side wall then that printing should be consistently oriented.

The apparatus of FIG. 1 comprises a dosage source 42 which is arranged to provide dosage forms to a dosage handler 60. For example, the dosage source may comprise or be arranged to accept one or more singulator hoppers 43, each singulator hopper being arranged to release one dosage form at a time under control of a controller 50. In this way multiple batches of dosage forms may be loaded for analysis, each in a separate singulator hopper 43 containing perhaps tens to hundreds of such dosage forms, and the controller can then provide automatic, scheduled processing of these batches. Each such batch, or each of two or more of the singulator hoppers, may conveniently contain a different type of dosage form, for example different in terms of any of geometry (size, shape etc.), pharmaceutical content, markings, colour, and so forth. The described apparatus is particularly beneficial in being able to handle such different types of dosage forms without any particular physical change or modification to the apparatus, so that multiple different batches of dosage forms can be processed in a single operating session without user intervention.

The singulator hopper or hoppers may be arranged to deliver each dosage form to a feed mechanism 44. The feed mechanism 44 could for example comprise a carousel having multiple peripheral apertures each for receiving one such dosage form 12, the carousel rotating to transfer received dosage forms to be released one at a time from the dosage source 42 to the dosage handler 60.

The dosage handler 60 receives a series of dosage forms of the same type or batch from the dosage source 42, and is then automatically operated by the controller 50 to consistently set at least some aspects of the rotational state of each such dosage form for presentation at the test location 22 of the Raman analysis station 20 (for example alignment of a dosage axis of the dosage form into a preferred direction and/or orientation of the dosage form about that dosage axis). In this way, potential errors and variations in detected properties of the dosage forms which could otherwise arise due to inconsistencies in rotational state at the test location 22 can be minimised or reduced. To this end, the controller may comprise or be provided with alignment/orientation data 52 defining a predefined or preferred rotational state such as alignment and/or orientation for each type or batch of dosage forms which may be delivered to the dosage handler 60 by the dosage source, to be used as described in more detail below.

Following the optical analysis, the dosage handler 60 carries out an output operation. Typically, the output operation should permit each optically tested dosage form to be uniquely and accurately located or identified for possible further testing or analysis. To this end, the dosage handler 60 may deposit each tested dosage form in a different cell of an output tray 45, in such a manner that the cell used for that particular dosage form can later be identified either manually or as part of a further automatic process.

Figure 2:
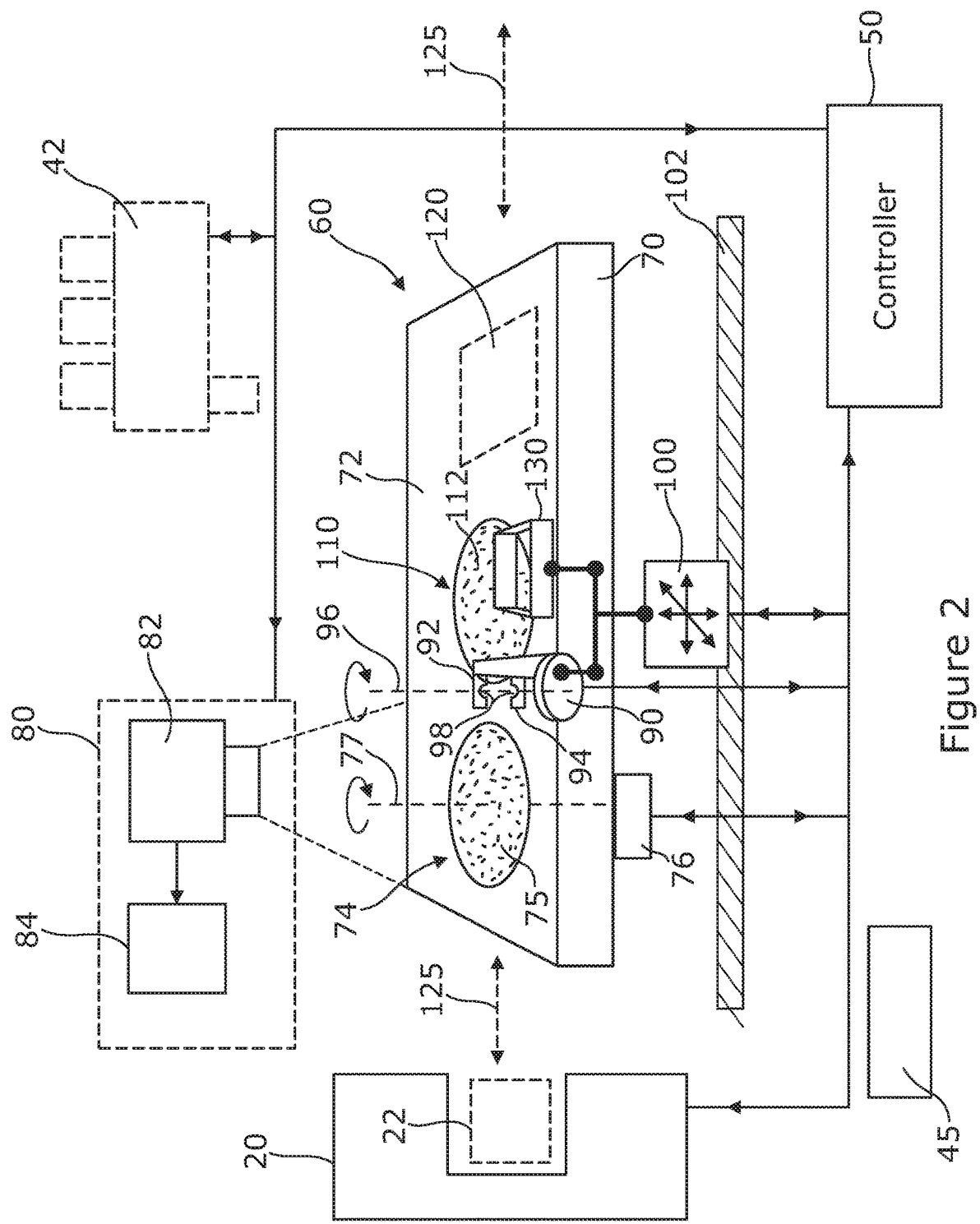
FIG. 2 illustrates in more detail some aspects of the dosage handler of FIG. 1.

FIG. 2 illustrates schematically how the dosage handler 60 of FIG. 1 may be implemented to provide the desired improved consistency of alignment and/or orientation in optical analysis of a plurality of dosage forms of a single type or batch. The dosage handler 60 comprises a handling table 70 which provides a table surface 72 on which each dosage form 12 delivered from dosage source 42 can be manipulated. The table surface 72 may preferably be level, i.e. substantially horizontal. The table surface 72 may be smooth, or may be textured in some way, either in one or more regions or across the whole table surface 72. For example, a surface texture may be provided which permits a dosage form 12 to be pushed or slid across the table surface 72 but which prevents or reduces unwanted rolling or other movement of a dosage form. Suitable surface textures may for example comprise small repeated protrusions such as in pyramid or conical forms, small repeated indentations or dimples and so forth. Such features may for example have a height or depth, and a repeat period, of less than about 1 mm.

The dosage handler 60 illustrated in FIG. 2 comprises a rotation stage 74 having a rotation stage surface 75 which is arranged to receive and rotate a dosage form 12 to a predetermined, preferred alignment, for subsequent grasping for carrying to and analysis by Raman analysis station 20. The rotation stage surface 75 may typically be flush with, or form part of, the table surface 72 of the handling table (and therefore typically also level or substantially horizontal) to enable a dosage form 12 to be pushed across the table surface 72 and onto the rotation stage surface 75 as discussed in more detail below. The rotation stage surface 75 is arranged to rotate about a rotation stage axis 77 which is substantially perpendicular to the rotation stage surface and the table surface, so typically approximately vertical if the table surface is approximately horizontal. In other words, the rotation stage used to rotate the dosage form about a typically vertical axis to achieve the desired rotational alignment about that axis.

To achieve the preferred alignment, the dosage handler 60 also comprises a machine vision system 80 to detect at least some aspects of rotational state of the dosage form for example when present on the rotation stage surface 75, and to pass the detected aspects to the controller 50 so that the preferred alignment of the dosage form can be achieved by rotating the rotation stage 74 by suitable control of a rotation stage motor 76 (which may be considered to be comprised in the rotation stage 74 in some embodiments). For example, the machine vision system 80 may detect a starting alignment of a dosage form on the rotation stage surface, and pass this starting alignment to the controller which then rotates the rotation stage to bring the dosage form into the preferred alignment. In other embodiments the machine vision system may monitor the alignment of the dosage form as the rotation stage is rotated, and the controller is then arranged to stop the rotation when the preferred alignment is achieved.

The machine vision system 80 may comprise at least one camera 82 having a field of view comprising at least part of the rotation stage surface 75, typically looking downwards at the rotation stage, and a machine vision processor 84 arranged to receive one or more images of a dosage form 12 located on the rotation stage surface and to detect desired properties of the dosage form 12, including aspects of rotational state such as alignment and orientation, from the images. Although depicted as a separate entity in FIG. 2, the machine vision processor 84 may be provided as part of the controller 50 if desired.

The machine vision processor 84 may detect other properties of the dosage form 12 in addition to aspects of rotational state, for example location of the dosage form on the rotation stage surface 75, and positive or negative identification of the dosage form as being of a particular type or from a particular batch, for example using features such as those described above which may include shape, size, printed markings, surface embossing and debossing markings, colour areas and so forth, and pass such detected properties to the controller 50, analyser 34, personal computer 36 or other suitable element. For example, the controller 50 may control the dosage handler 60 to handle a dosage form differently depending on what type of dosage form is detected, for example orienting the dosage form in a manner specific to that type for optical analysis.

The machine vision system 80 may also be used to determine dimensions of a dosage form (it may be required to check these against desired dimensions), such as a diameter of a dosage form of round plan view, or more specific length and width dimensions of dosage forms of other plan forms such as ellipses, rectangles, or capsule forms. Other suitable measures could include plan view surface area. Thickness of a dosage form between two largely planar opposing surfaces, such as thickness of a tablet may also be determined by the machine vision system, although this may require some specific manipulation of the dosage form to ensure that the dosage form edge is suitably presented to the camera 82. In some cases the machine vision system may take sufficient dimensional and/or area measurements to enable a volume of the dosage form to be calculated.

For a particular type or batch of dosage form, the preferred alignment may be defined (for example in the alignment/orientation data 52 available to the controller) with reference to a dosage axis of the dosage form, which can be predefined and at least implicitly recognised from imagery of such a dosage form using the machine vision system 80. Rotation of a dosage form on the rotation stage to a preferred alignment then equates to rotation of a predefined dosage axis of the dosage form into alignment with a target axis parallel with the rotation stage surface, where the target axis may typically be fixed with respect to the dosage handler 60 or one or more other parts of the apparatus 10.

Figure 3A:
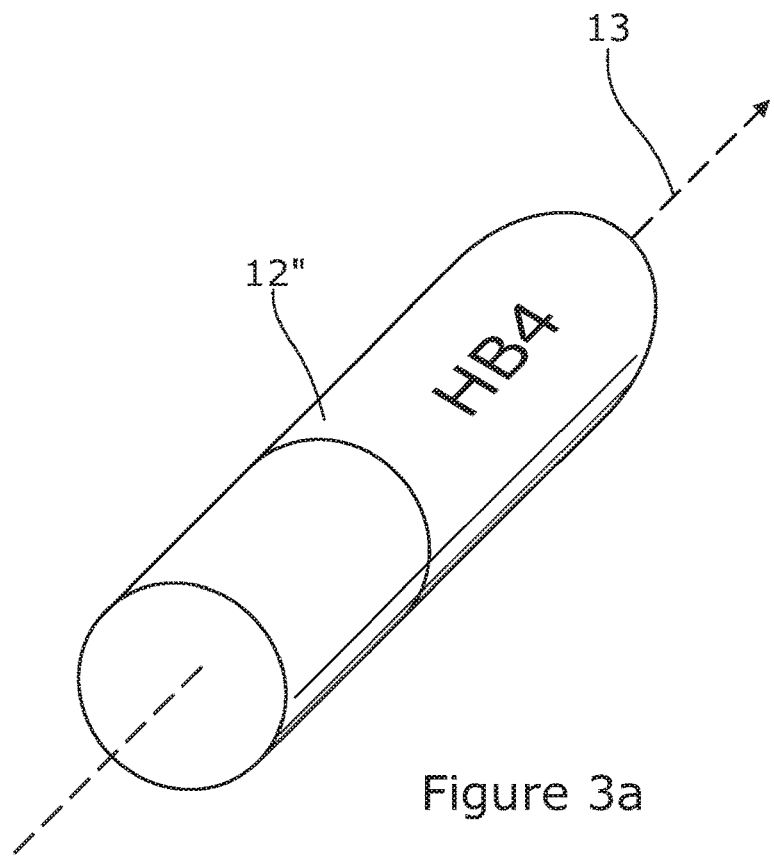
FIG. 3a & 3b depicts dosage forms which could be handled and analysed using the apparatus of FIGS. 1 and 2, and associated dosage axes which may be identified by a machine vision system of the apparatus.

FIG. 3a shows how a dosage axis 13 and therefore a preferred alignment (i.e. rotational orientation) of a dosage form may be defined. In this case, an essentially cylindrical capsule 12" is shown as having a dosage axis 13 which corresponds in this case to the axis of rotational symmetry of the cylinder. A preferred alignment of this capsule may be when the dosage axis 13 is parallel with a target axis (not shown in the figure). If the capsule 12" or other dosage form is not symmetrical under a reversal of direction or reflection along this dosage axis, for example having different coloured ends or other asymmetric features as shown in the figure, then the preferred alignment may require the dosage axis to specifically be parallel or anti-parallel to the target axis.

Because the alignment of the dosage form on the rotation stage may determine how the dosage form is grasped for carrying to the test location, selection of the dosage axis may also take into account the expected stability of hold by a gripper when grasped along, or in an orientation defined relative to, this axis.

If additionally the capsule 12" includes features which make it asymmetric in rotation about the dosage axis 13, such as the printed characters shown in the figure, then as well as rotating the dosage axis to a preferred alignment it may be desirable to rotate the dosage form about the dosage axis, or another axis substantially parallel to the surface of the rotation stage, to a preferred orientation of rotation, for example using the gripper described in more detail below.

Figure 3B:
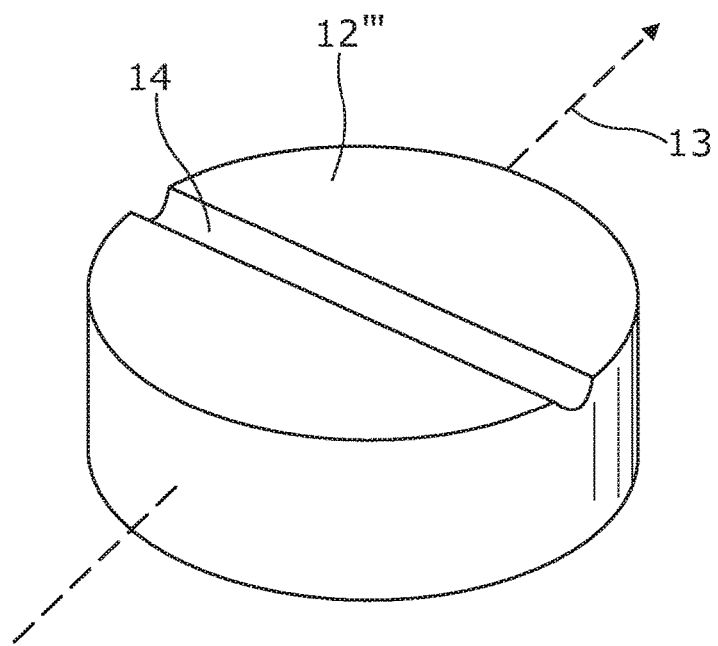

FIG. 3b shows another example of how a dosage axis 13 may be defined, in this case for a tablet 12''' having an debossed snap line feature or break line 14 on one of the two opposing circular faces of the tablet 12'''. In this case, a preferred orientation of rotation about the dosage axis could be to have the snap line facing in a particular direction, for example either upwards or downwards, or possibly either facing to the left or right in the figure.

Referring back to FIG. 2, the dosage handler 60 also comprises an element for moving the rotated dosage form to the testing location. In FIG. 2, this element is provided by a gripper 90 which is arranged to grasp the dosage form 12 after rotation into the preferred alignment using the rotation stage, and to carry the grasped dosage form to the testing location 22 of the Raman analysis station 20, with these actions being carried out under control by the controller 50.

In being carried from a position where the dosage form on the rotation stage is grasped by the gripper, to a position where the dosage form is presented for analysis at the testing location 22, the alignment and optionally other aspects of the orientation of the dosage form may remain fixed, or they may be changed in a controlled and known manner so as to achieve a consistent alignment and/or orientation of the dosage form at the testing location. However, following optical analysis there will usually be little or no need to retain a known or accurate alignment or orientation of the dosage form during the subsequent output operation.

The gripper 90 may also be arranged to rotate a grasped dosage form about a gripper rotation axis 96, which may for example be an axis parallel to the rotation stage surface 75 (so typically a horizontal axis), to a preferred orientation of rotation. This may be achieved by using the gripper to grasp the dosage form, lift the dosage form above the rotation stage surface 75, rotate the dosage form, and return the dosage form to the rotation stage surface 75, and release the dosage form. Such a sequence could be used if it is preferred for the gripper to return to another rotation and/or translation condition before grasping the dosage form again for carrying to the testing location. Alternatively, the gripper could rotate the dosage form following grasping and lifting, without again placing the dosage form onto the rotation stage surface, for example as part of the movement to carry the dosage form to the testing location, or indeed at the testing location. As another alternative, such lifting and/or replacing of the dosage form by the gripper could take place on one or more other parts of the table surface away from the rotation stage, and in some arrangements or operations there may be no need to lift the dosage form before carrying out the rotation, for example if the rotation is about an axis of symmetry of a cylindrical form.

Typically, the gripper 90 may comprise opposing jaws 92, 94 which are arranged to close towards each other and onto a dosage form to thereby grasp the dosage form. Although the dosage axis may be defined in various ways in order to fulfil the requirement of rotation using the rotation stage to a preferred alignment as discussed above, the dosage axis may conveniently be defined as an axis along which the gripper jaws approach so as to close onto the dosage form for grasping and carrying the dosage form to the test location.

As illustrated in FIG. 2, the gripper rotation axis 96 may also be parallel to the axis along which the gripper jaws close, and therefore also the target axis mentioned above which is the same as the dosage axis when the dosage form is in the preferred alignment on the rotation stage 74.

Each gripper jaw 92, 94 may be designed to function in a satisfactory manner for all anticipated dosage forms without need to customise shape or change gripper jaw for any particular dosage form or class of dosage form. To this end, each gripper jaw may comprise a concave surface 98, these concave surfaces being opposed to each other and presented to a dosage form for grasping the dosage form when the jaws approach each other. Each concave surface may have a suitable radius of curvature for providing a more secure grasp of a typical dosage form to be handled, for example with a radius of curvature of between about 3 and 10 mm.

More generally, methods of operating the apparatus may comprise the dosage handler delivering each of a plurality of dosage forms of a first geometry (for example shape, size etc.) to the test location for optical analysis, and then delivering each of a plurality of dosage forms of a second, different geometry to the test location for optical analysis without changing or modifying the gripper jaws.

In order to control the gripper to rotate the dosage form to a preferred orientation of rotation, for example as defined by the alignment/orientation data 52, the machine vision system 80 is also arranged to detect orientation of rotation of the dosage form for example about the gripper rotation axis and/or the dosage axis and to pass this detected orientation to the controller. This could be done either as a starting orientation from which the controller can determine a required amount of gripper rotation, as an ongoing detection of the orientation as gripper rotation takes place, or in other ways.

Translational movement of the gripper 90 as a whole is provided by multi-axis staging 100, typically having three translational axes so as to enable the gripper to move to a position on the table to grasp as dosage form, to lift the dosage form from the table, to carry the dosage form to the test location 22, and to complete the output operation. To this end, the machine vision system 80 is also arranged to detect a lateral position of the dosage form on the rotation stage, and to pass the detected lateral position to the controller for controlling the gripper to grasp the dosage form in the detected lateral position both by suitable control of the multi-axis staging 100 and of the gripper jaws 92, 94.

The gripper may be arranged such that both gripper jaws move relative to the multi-axis staging 100 as the jaws close towards each other. Alternatively, one jaw may be stationary relative to the staging 100 (for example the distal jaw 92 which is further from the staging 100 in FIG. 2), while the other jaw is arranged to translate relative to the staging (for example the proximal jaw 94 which is closer to the staging 100 in FIG. 2).

In addition to the rotation stage 74 and rotation stage surface 75, the handling table 70 may comprise other structures and areas for handling, analysing and otherwise processing a dosage form. For example, as illustrated in FIG. 2, the handling table 70 may also comprise a weighing scale 110 comprising a weighing scale surface 112. The weighing scale surface 112 is preferably flush with or forms part of the table surface 72, so that a dosage form can be slid or pushed across the table surface 72 and onto the weighing scale surface 112. The weighing scale is coupled to the controller 50 so that the weight of a dosage form can be received from the weighing scale, for example for reporting to the personal computer 36 or other parts of the apparatus. The determined weight of a dosage form can be used, for example in conjunction with other properties determined by the machine vision system, and/or analyser 34 to help determine whether the dosage form meets particular required specifications, or to help determine if the dosage form is of the expected type or from the correct batch.

Although depicted as separate in FIG. 2, in some embodiments the weighing scale may be incorporated into rotation stage.

The handling table surface 72 as shown in FIG. 2 also comprises a drop zone 120, which is a region of the table surface 72 onto which the dosage form source is arranged to deposit a dosage form for manipulation and analysis. Providing such a drop zone 120 which is separate from the weighing scale surface means that impact of a dosage form dropping onto the drop zone 120 does not adversely affect the accuracy of the weighing scale. Once the dosage form has been dropped onto the drop zone 120 by the dosage source, it can be moved for example by sliding or pushing for subsequent weighing by the weighing scale 110.

Some or all of the rotation stage surface 75 could in principle be used as the drop zone, but robotic layout and workflow considerations make it advantageous for these areas to be kept separate.

The dosage handler 60 may also comprise an element for pushing or sliding a dosage form across the table surface 72.

In FIG. 2 this is illustrated as a box slider 130 which, in the plane of the table surface 72 or from a top view surrounds a dosage form when in position to or in the process of pushing or sliding the dosage form, although other forms of slider which do not necessarily surround the dosage form could be used. The illustrated box slider 130 shown in FIG. 2 provides a closed rectangular perimeter around the dosage form to be moved, but other forms can be used subject to the slider being useful for accurate positioning of a dosage form where required on the table surface 72. The box slider of FIG. 2 has lateral dimensions of about 30 to 60 mm along each side.

In particular the box slider 130 may be controlled by the controller 50 to move to the drop zone 120 so as to receive a dosage form within the box slider 130 from the dosage source 42. The box slider is then controlled to move the received dosage form to the weighing scale surface 112 for weighing, and then on to the rotation stage surface 75 for alignment and/or orientation before being transported by the gripper 90 to the test location 22.

In order to leave a dosage form at the rotation stage surface 73, the box slider 130 is provided with an axis of translation perpendicular to the table surface 72, typically in a vertical direction, so that it can be lifted sufficiently to clear the dosage form. Additionally, the box slider 130 will typically be provided with two axes of translation so as to be able to move a dosage form to a variety of locations on the table surface 72 as may be required by the manipulation process to be carried out.

Conveniently, the box slider may be mounted to the same multi-axis staging 100 as the gripper 90. For constructional efficiency and use, the dosage handler 60 may then be arranged such that the drop zone 120, weighing scale surface 112, and rotation stage surface 75 are generally disposed in that order along a process axis 125 of the dosage handler 60 generally indicated in FIG. 2, and the test location 22 of the Raman analysis station may then also be disposed generally further along the same process axis 125 from the rotation stage surface 75. The multi-axis staging 100 used to move the position of the gripper 90 may also provide the required movement of the box slider 130 along the process axis 125 between the drop zone 120, the weighing scale 110 and the rotation stage 74.

The process axis 125 may correspond to a principle axis of motion of the multi-axis staging 100, for example by movement of the multi-axis staging along a rail 102 or similar structure which extends along or parallel to the process axis 125. In practice, three separate axes of motion may be commonly provided to both the gripper and box slider by the multi-axis staging. In the arrangement of FIG. 2 these axes would provide movement along the process axis, in a perpendicular depth direction across the table surface, and vertically. However, in some arrangements one or more of these axes could be separately provided for each of the gripper 90 and the box slider 130, for example with each of the gripper and box slider being provided with separate vertical or separate depth control axes.

Figure 4A:
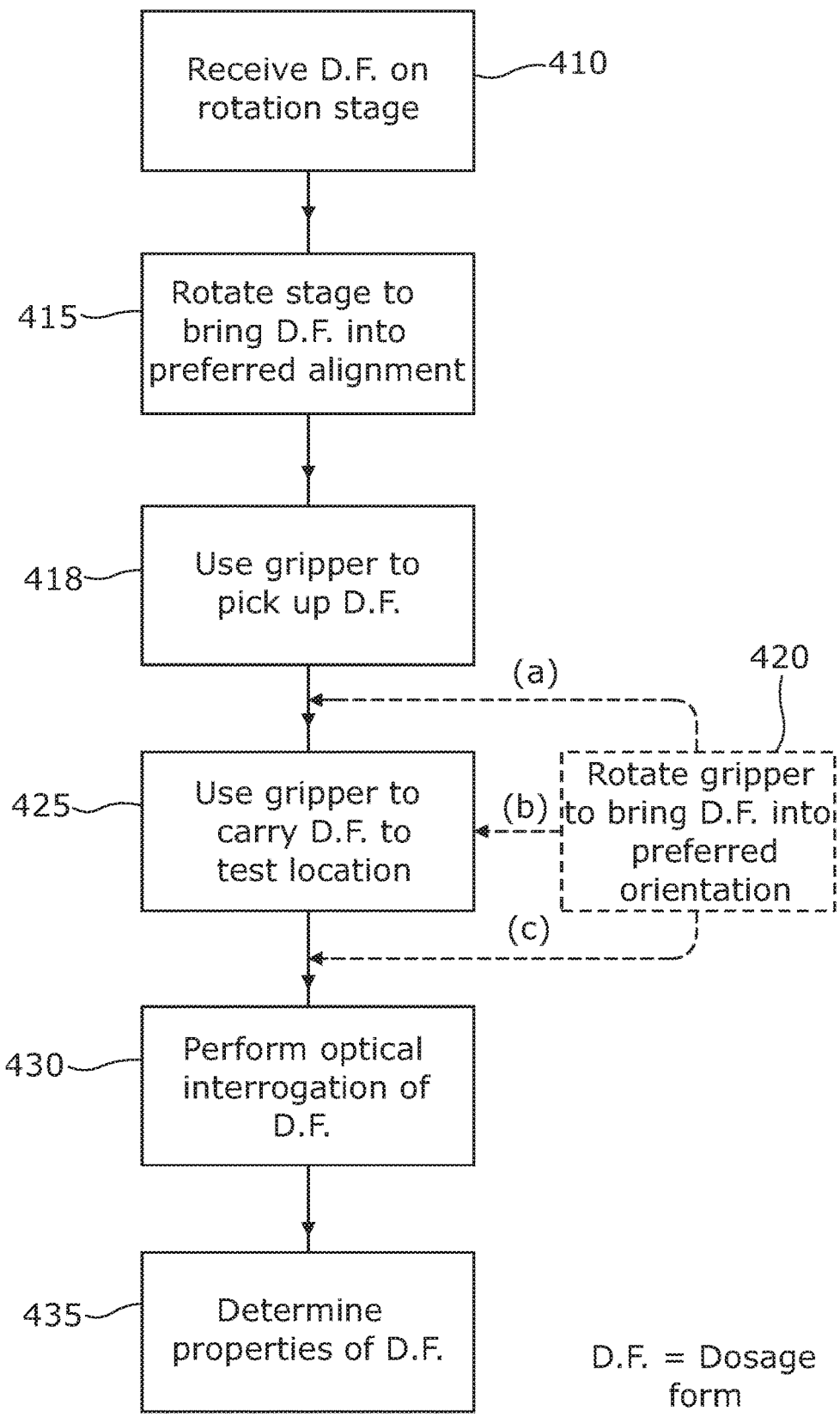
FIGS. 4a, 4b, 5 and 6 illustrate methods of operation of the apparatus of FIGS. 1 and 2.
Figure 4B:
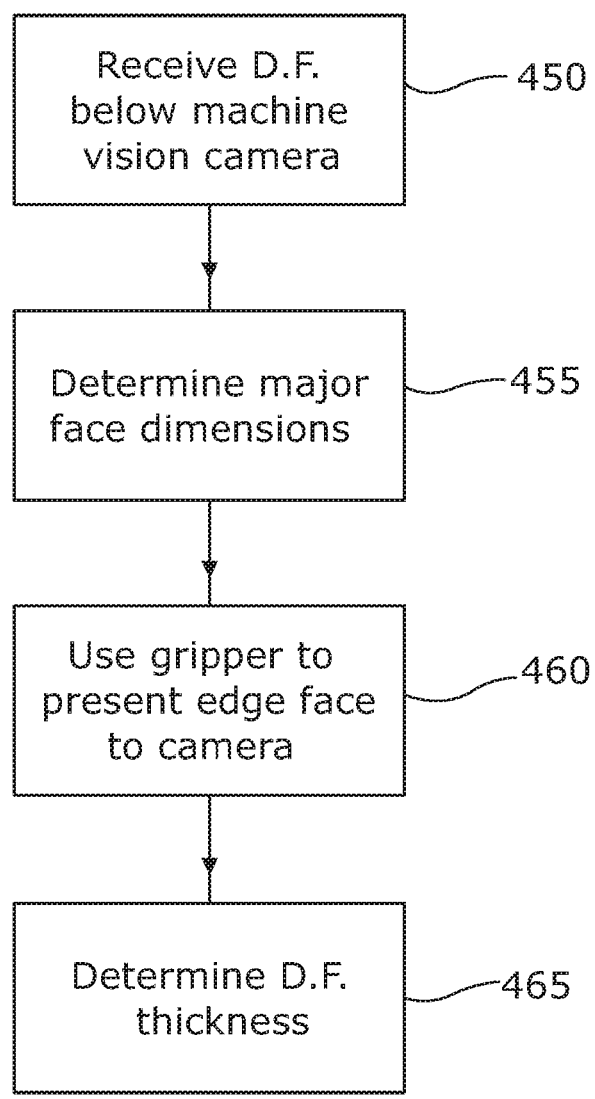
Figure 5:
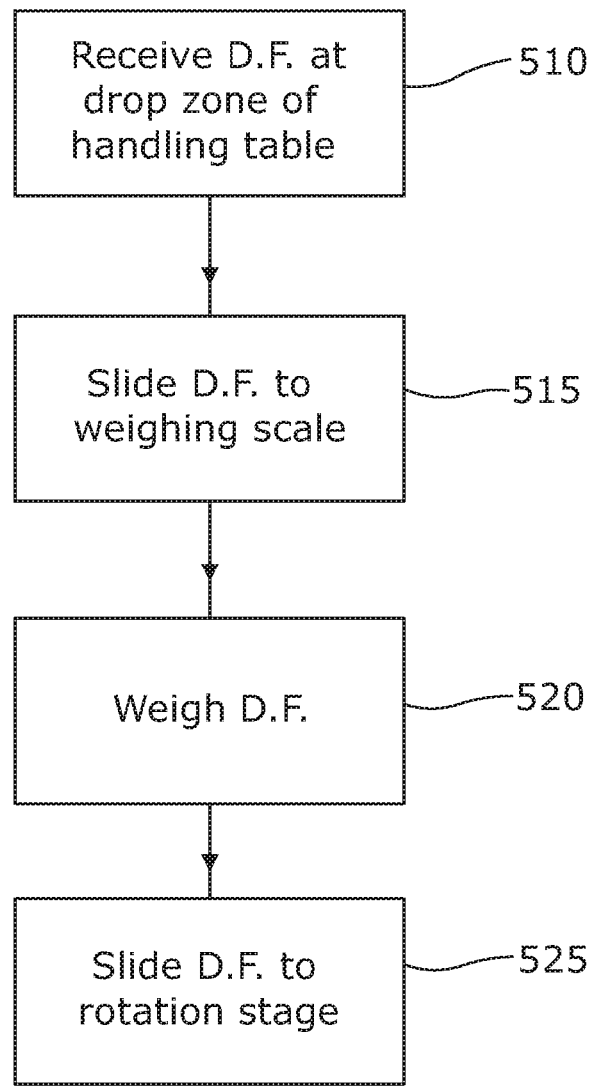

FIGS. 4a, 4b and 5 use flow diagrams to illustrate some ways in which the apparatus described above may be automatically operated, for example by controller 50, so as to present a dosage form in a consistent rotational state such as alignment and/or orientation at the test location 22 of the Raman analysis station 20 or other spectral or optical analysis arrangement. Although particular sequences of process steps are illustrated and discussed, subsets of these steps may be used without all of the other steps, and the steps need not necessarily be used in the described and illustrated order.

In step 410 of FIG. 4a, a dosage form is received on a rotation stage 74. The dosage form may be received on the rotation stage in various ways, for example as discussed above, and below in connection with FIG. 5.

At step 415 the rotation stage is rotated so as to rotate the dosage form about an axis of rotation 77 of the rotation stage, typically a vertical or substantially vertical axis, into a preferred alignment or orientation about that axis. As discussed above, the amount of rotation required to achieve the preferred alignment of the dosage form may be determined using a machine vision system 80 comprising a camera having a field of view which includes some or all of the rotation stage 74. The preferred alignment of the dosage form may be achieved by aligning a predefined dosage axis 13 of the dosage form which can be identified using the machine vision system with a target axis typically fixed with reference to non-moving parts of the apparatus such as the machine vision system.

The dosage form is then grasped using the gripper 90, in the preferred alignment, at step 418, and picked up from the rotation stage. The dosage form is then carried by the gripper 90 to the test location 22 of the optical analysis station, at step 425, for optical analysis at step 430. An optional step shown as step 420 in FIG. 4a may also be carried out after, or in some cases before, rotation of the dosage form to a preferred alignment using the rotation stage. This additional step comprises using the gripper 90 to rotate the dosage form about a gripper rotation axis 92 to a preferred orientation. The gripper rotation axis 92 is typically oblique or substantially perpendicular to the rotation stage axis 77, so may typically be horizontal or substantially horizontal, and/or parallel to a surface 72 of the rotation stage on which the dosage form is supported.

Rotation to the preferred orientation may for example take place in part or whole while the dosage form is still on or just above the rotation stage, and/or during movement to the test location, and/or on arrival at the test location, as demonstrated by the three alternative time points (a), (b) and (c) in FIG. 4a.

In this way, the preferred alignment and/or orientation of the dosage form is preserved, albeit with any known subsequent rotations due to controlled movement of the gripper, until an optical interrogation at the test location has been completed, following which the dosage form can be released from the grasp of the gripper.

Optical interrogation of the dosage form is carried out at step 430, and in particular this may be Raman interrogation to determine Raman spectral features, or other types of spectral or optical analysis as discussed elsewhere in this document. The optical interrogation may in particular be carried out in a transmission configuration, for example by directing laser probe light to a first surface region of the dosage form, collecting elements of the laser probe light scattered within the dosage form from a second surface region of the dosage form, the second surface region being on an opposite side of the dosage form from the first surface region, and detecting Raman or other spectral features in the collected light.

As already noted above, the dosage form may be presented using the gripper in the test location 22 at a particular fixed position and state of rotation (orientation/alignment) for the duration of optical testing, or may be moved/rotated between a number of discrete positions with optical testing taking place at each discrete position, and/or may be moved (including either or both of translational movement and rotation) with optical testing taking place during the course of that movement, such as in a scanning action.

Finally, properties of the dosage form are determined at step 435. Such properties may be chemical properties of the dosage form such as the presence or proportions of particular chemical species or forms, and such properties can be determined from the detected Raman or other spectral features. Various notifications and/or alerts can then automatically be generated for the attention of an operator of the apparatus, for example alerts indicating properties of one or more dosage forms lying outside preferred ranges.

By using a transmission geometry, and by using Raman spectral analysis, various useful chemical and constitutional properties of the internal bulk, rather than just from the surface regions of the dosage form, can be determined. However, such transmission analysis can be sensitive to the precise rotational state such as alignment/orientation of a dosage form in the test location 22, and by carrying out a suitable alignment/orientation using the rotation stage and/or gripper, and preserving that rotational state using the gripper (albeit with subsequent known rotations), more consistent results of the Raman spectral analysis can be achieved.

The gripper may be used for other operations and actions in addition to those described above and illustrated in FIG. 4a. For example, it may be required to "flip" a dosage form over so that a preferred face of the dosage form is facing upwards and towards the camera 82, either before or after the dosage form is rotated to the preferred alignment. Such an operation could enable the machine vision system 80 to better determine or control a correct alignment of the dosage form, for example if suitable markings are only seen on one main face of a dosage form, in which case such a flip operation may be undertaken by the gripper before the rotation stage operation. In another example as discussed below the gripper may be used in presenting an edge of a dosage form to the machine vision system in order to assist in determination of a thickness of the dosage form.

The machine vision system 80 may be used to obtain various dimensional measurements of a dosage form when the form is lying on the rotation stage and/or held by the gripper. Typically, the machine vision system may comprise a camera 82 having a downward view onto the rotation stage as shown in FIG. 2. If the dosage form has two opposing major faces, as is typical for tablets and some other forms, then although plan view dimensions may easily be obtained when the dosage form is lying flat with such a major face on the rotation stage using a downward view camera, it may also be desirable for the machine vision system 80 to determine a thickness between the two opposing major faces, and this dimension will be hidden from the camera in such a view. Such a dosage form may typically be a tablet or similar comprising two opposing circular faces with a side wall of approximately constant width extending between these faces, but other face shapes and geometries may be used.

To this end, the gripper 90 may also be used, under control of the controller and with use of the machine vision system 80, to present an edge face or side wall of the dosage form to the camera 82 of the machine vision system 80 so that a thickness of the dosage form can be determined, for example by the machine vision processor 84. This may be carried out before or after step 415 in FIG. 4a, for example depending on whether a particular rotational state of the dosage form is required for it to be picked up by the gripper.

In some examples, the gripper may be used to lift and rotate the dosage form, for example through 90 degrees, before replacing it on edge on the rotation stage. The gripper then releases the dosage form and can also be moved out of the way in order to provide the machine vision system with a clearer view of the dosage form. In other examples, the gripper may rotate the dosage form, for example through 90 degrees, to present an edge view to the machine vision system while retaining grasp of the dosage form and without placing the dosage form on edge on the rotation stage. For some designs of gripper 90 particular rotations might be required to ensure that a sufficiently clear view of the dosage form edge is still obtained.

In either case, the machine vision system is then used to acquire and output suitable dimensional data of the dosage form from the edge view in order to determine a thickness of the dosage form.

If the dosage form is placed on edge onto the rotation stage for determination of thickness following a rotation step 415 of FIG. 4a, then it may be possible to use the gripper to pick up the dosage form again from this position and proceed with steps 425, 430 and 435 of FIG. 4a, and optionally also step 420. However, the process of placing the dosage form on edge may instead require the dosage form to be returned to a state on the rotation stage where a major face is flat on the stage, either by direct handling using the gripper, or knocking the dosage form over in some manner, such that rotation of the stage under step 415 may needed to be repeated after the edge thickness determination.

Some ways in which the above dimensions measurements may be implemented are shown in FIG. 4b. At step 450 a dosage form having opposing major faces separated by an edge face is received beneath the machine vision system camera 82, which in the context of FIG. 4a may be step 410 where the dosage form is received on the rotation stage, but may be on some other surface or part of handling table 70. At step 455 the machine vision system camera 82 is used to detect dimensions of the major face of the dosage form which is in plan view beneath the camera. Such dimensions could be a diameter of a circular dosage form, length and width dimensions of an ellipsoidal or rectangular tablet, a plan view surface area, and so forth. If the dosage form is also being manipulated according to a scheme such as that of FIG. 4a then step 455 may take place before or after s step 415 of rotating the dosage form into a preferred alignment.

At step 460 the gripper 90 is used to grasp the dosage form and rotate the dosage form to present the edge face to the machine vision system camera 82. For example a portion of the edge face closest to the camera may be rotated to be substantially horizontal, but other angles of presentation relative to the camera could be used which give sufficient accuracy of measurement. The gripper might then either put down the dosage form on edge and move away to give the machine vision system a clear view of the dosage form, or might retain grip of the dosage form if this still provides a sufficiently clear view. At step 465 the machine vision system is used to detect a thickness of the dosage form using the visible width of the edge face. If the dosage form is also being manipulated according to a scheme such as that of FIG. 4a then step 460 may be followed by repositioning the dosage form to lie on a major face before carrying out, or carrying out again rotation step 415 if necessary, or step 465 might be followed by step 425 (and optionally step 420) in which the dosage form is carried to the test location without necessarily needing to be put down by the gripper again on the rotation stage.

FIG. 5 shows steps which may be implemented automatically, for example under control of a controller 50, in order to provide a dosage form to the rotation stage 74 so that a method such as that of FIG. 4a can be carried out.

In step 510 a dosage form is received at a drop zone 120 of a handling table 70 which also comprises the rotation stage 74. The handling table 70 may also comprise a weighing scale 110, and the rotation stage and weighing scale may be flush or form part of the handling table such that a dosage form can be pushed or slid across the handling table between these stations. The drop zone is provided separately on the handling table 70 to the weighing scale if provided, so that dropping of the dosage form onto the handling table does not affect subsequent performance of the weighing scale which could take some time to return to an equilibrium if the dosage form was dropped directly onto the weighing scale, thereby slowing down the handling and optical analysis process.

The dosage form may be delivered to the drop zone 120 by a dosage source 42 as described elsewhere in this document, which may itself comprise or be arranged to accept one or more singulator hoppers 43 each capable of carrying a batch of tens or hundreds of dosage forms of the same type and to be tested in the same way, and of delivering one such dosage form at a time to the drop zone.

At step 515 the dosage form received at the drop zone is moved by sliding or pushing across the handling table onto the weighing scale 110, if provided. The dosage form is then weighed at step 520, and then moved by sliding or pushing across the handling table onto the rotation stage at step 525. At this point, the steps of FIG. 4a may then be carried out.

The sliding or pushing of the dosage form across the handling table may be carried out by a slider element, for example the box slider 130 illustrated in FIG. 2. Such a box slider which surrounds the dosage form in all horizontal directions permits the dosage form to be dropped by the dosage source 42 in step 510 without risking the dosage form bouncing away from an expected location or off the handling table altogether. The box slider form then also permits the dosage form to be moved accurately in any horizontal direction under control of the controller 50, to any desired position for example at the centre of the weighing scale or the centre of the rotation stage.

The described apparatus may also be used to carry out an automated series of tests on the same or a series of dosage forms of the same type. Such a series of tests can be used for example to determine operating characteristics of the apparatus, such as accuracy and repeatability of the presentation of a dosage form at the test location 22, and therefore also of the resulting optical analysis and determined properties of such a type of dosage form. To this end, the described apparatus may for example be used to carry out a method as outlined in FIG. 6.

Figure 6:
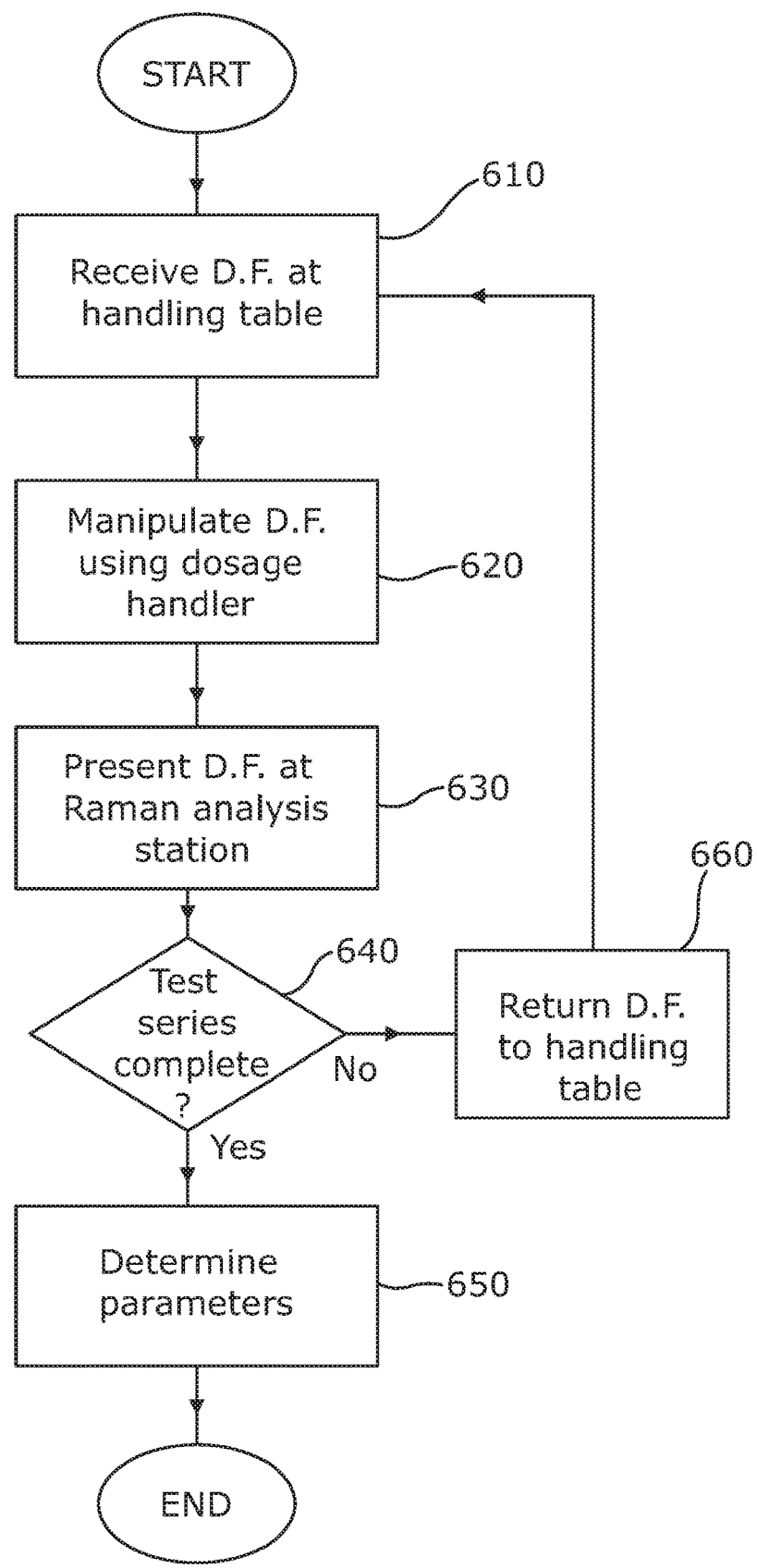

In FIG. 6, a dosage form is received at the handling table 70 in step 610, for example at a drop zone 120 of the handling table. The dosage form is then manipulated using the dosage handler apparatus at step 620, for example including use of one or more of the box slider 130, weighing scale 110, rotation stage 74, gripper 90, and multi-axis staging 100 as described above. The dosage form is then presented at the test location 22 in step 630 in one or more preferred rotational states (combinations of orientations and alignments as required) and/or translational positions by the gripper 90 for optical interrogation by detection of Raman spectral features using the Raman analysis station 20. As discussed above, such rotational states and/or positions may include just a single such rotational state and position, or movement between multiple such configurations with optical analysis being carried out at each such configuration and/or continuously during such movement in the form a scanning operations.

If the series of tests is complete at decision point 640 then the data received from the series of optical interrogations may be analysed to determine one or more parameters of the handling, presentation and analysis process at step 650, but otherwise the dosage form may be returned to the handling table 70 in step 660, for example using the gripper 90 to return the dosage form to the drop zone 120, following which the steps of manipulation and presentation to the Raman analysis station 20 are repeated using the same dosage form.

Instead of handling and presenting the same dosage form each time to the Raman analysis station 20, a presented dosage form could be discarded and a new dosage form of the same type used for the next test sequence of FIG. 6. Instead of presenting a dosage form each time in the same orientation, alignment and position, the dosage handler could instead present a dosage form in a range of different such configurations.

The step 650 of determining parameters of the handling, presentation, and analysis process could take various forms. If a dosage form is presented in the Raman analysis station 20 each time using a supposedly identical rotational state, alignment and position, then the parameters may comprise one or more parameters representing measures of variance of a property of the dosage form such as the absolute content of an active pharmaceutical ingredient under these supposedly identical configurations.

If aspects such as rotational state and position of the dosage form at the time of optical interrogation are varied from one presentation to the next in order to test a range of such aspects, then the parameters determined in step 650 may represent how adjusting such aspects affects the results of the optical analysis. Such parameters or results can then be used to design an improved or optimised scheme for presenting dosage forms of the same or similar types at the test location 22.

The described apparatus can therefore be used to test the impact of variance and determine precision of the results of the optical measurements due to various different factors including variance in the handling and presentation of the dosage forms and variance in the optical measurements. The described apparatus can also be used to establish an improved or optimised scheme or handling and presentation of the dosage forms.

An apparatus 10 as described above and arranged to carry out handling and analysis of pharmaceutical dose forms as discussed may typically be capable of carrying out Raman spectral interrogation of a single dosage form in around a few seconds to a few tens of seconds, with this time period depending on the required signal to noise ratio of Raman spectral feature detection and consequent accuracy of determined chemical properties, on what power level of laser beam irradiation of each dosage form is acceptable, and other factors such as the types of optics and optical detectors used. Consequently, the dosage handler should be arranged to handle a series of dosage forms at the same rate or faster in order to make best use of the optical analyser. For example, if the dosage source can be loaded with ten singulator hoppers each carrying a hundred dosage forms then around a thousand dosage forms may easily be analysed fully automatically within a few hours, with the improved accuracy of optical analysis resulting from aspects of the invention discussed above.

Some aspects of the described apparatus and methods may be implemented using computer program code executing on one or more suitable computer systems. Such computer systems will typically comprise one or more microprocessors to execute such computer program code, memory to store such programs and related data, and suitable input and output facilities including for example wired or wireless data connections, non-volatile storage, visual displays, and input device such as keyboards and mice.

The controller 50 for example may comprise one or more suitable computer systems programmed to carry out the described operations by control of the dosage source, gripper, rotation stage, multi-axis staging and other components in response to data received from the machine vision system, weighing scale, analyser, and other sources. Some or all of the image and data processing aspects of the machine vision system may be implemented in a separate computer system or may be implemented within the same computer system or systems used to provide the data processing required of the controller 50. In some embodiments, the machine vision system may make use of the LabVIEW software (Laboratory Virtual Instrument Engineering Workbench) provided by National Instruments of Austin, Tex., to implement aspects such as identification of a particular type of dosage form, and various aspects of position and orientation of a dosage form.

The analyser may similarly be implemented using one or more computer systems using suitable software to receive a spectral data signal from the detector 32, analyse and process that spectral data signal in various ways for example to reduce noise, transform into desired forms, and determine or measure particular spectral features, and to match detected spectral features with those of known or expected components or characteristics of the dosage form under test. Libraries of spectral features which may be used for such comparisons are available for example from S.T. Japan or Sigma-Aldrich.

Figure 7:
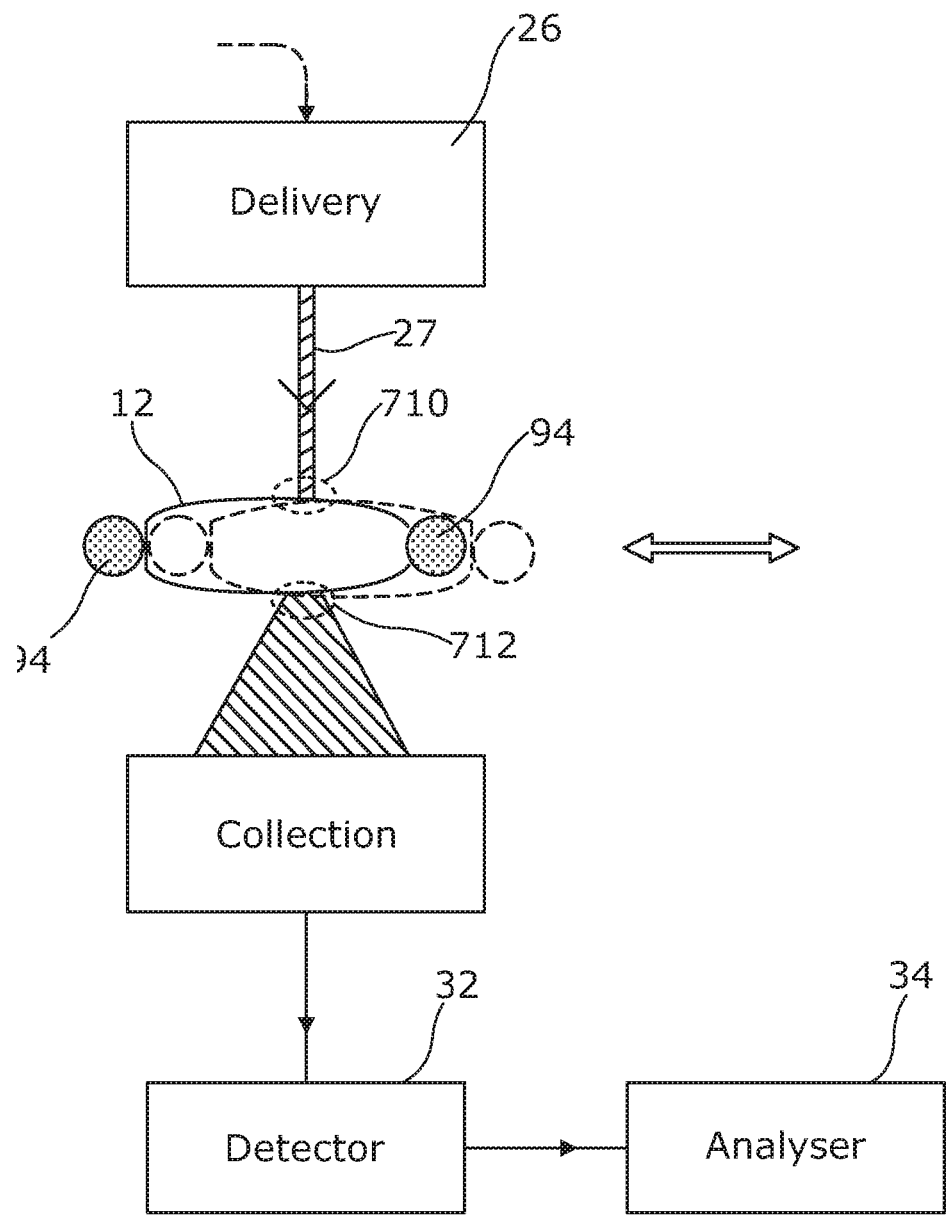
FIGS. 7 and 8 show how a dosage form may be presented at a test location of the Raman analysis station of FIGS. 1 and 2 with a range of alignments, the alignments differing in translation and/or rotation of the dosage form.

It has been discussed above how the gripper 90 may be used to move a dosage form 12 during presentation in the test location, with multiple optical measurements being taken across a range of alignments (variations in translational position and/or rotational orientation) of the dosage form so as to obtain a more representative optical measurement of the dosage form. To this end, FIG. 7 illustrates a dosage form 12 which has been grasped by the gripper, for example while lying on the rotation stage 74 or other part of the handling table surface 72, and which has been carried by the gripper 90 to the test location 22 provided within the Raman analysis station 20. These and other actions and motions by the gripper 90 may be effected by a controller such as controller 50 depicted in FIGS. 1 and 2, in combination with suitable motion providing elements such as the multi-axis staging depicted in FIG. 2.

More particularly, FIG. 7 depicts the delivery optics 26 and collection optics 30 already described above, with the dosage form 12 being located at a test location 22 between the two. The delivery optics 26 are then arranged to direct a beam of probe light 27 to a first surface region 710 of the dosage form, and the collection optics 30 are arranged to receive probe light from a second surface region 712 of the dosage form following scattering, or more particularly forward scattering, through the dosage form 12 from the first surface region to the second surface region.

In particular, the first surface region 710 and second surface region 712 may be on opposite sides or opposite faces of the dosage form 12, for example on respective first and second surfaces 40 and 41 as already depicted in FIG. 1, such that the dosage form is tested using a forward scattering or transmission configuration, although other configurations may be used such as other configurations discussed above.

The detector 32 already illustrated in FIG. 1 and discussed above is arranged to receive the collected probe light from the collection optics 30 and to detect Raman spectral features in the collected probe light, for example Raman spectral features representing the magnitudes of a number of Raman spectral peaks, or more generally a full Raman spectrum representing a detected intensity or power as a function of wavenumber or wavelength. This data is then passed to the analyser 34, also discussed above, which is arranged to determine one or more properties of the dosage form under test using the Raman spectral features, such as relative concentration of a particular constituent of interest such as an active pharmaceutical ingredient.

In some embodiments, a particular dosage form 12 is positioned at the test location and held stationary in a single configuration or alignment between the delivery and collection optics while Raman spectral features are measured, and the Raman spectral features for that single alignment are then used for determining one or more properties of the dosage form. However, the inventors have noted that there may be several benefits in moving the dosage form within the test location while under test so that Raman spectral features are detected for a plurality of different such alignments or configurations. Such measurements of Raman spectral features may be taken at each of a plurality of discrete and typically stationary alignments, during one or more movements of the dosage form, or a combination of the two. Typically, all such alignments may be used for obtaining Raman spectral features without removing the dosage form from the test location, but in some embodiments in may be desirable or appropriate to remove the dosage form from the test location between some alignments or groups of alignments. One such situation could be, following use of one or more alignments, to replace the dosage form on a surface such as the table surface 72 so as to rotate the gripper, pick the dosage form up again with the gripper in the rotated position, invert the dosage form using the gripper, and present the dosage form in the test location in the inverted (upside down) state for use of one or more further alignments.

Different alignments or configurations of the dosage form at the test location 22, whether discrete such alignments, or continuous movements through ranges of such alignments, may be provided in particular by rotation of the dosage form about one or more chosen axes, translation in one or more directions, or a combination of the two. Such changes in alignment of the dosage form at the test location result in corresponding changes in the positions on the dosage form of one or both of the first and second surface regions 710, 712, and therefore changes in the scattering paths of probe light between the first and second surface regions, and therefore also changes in the representative volume of the dosage form being tested in each alignment.

Moving the gripper to present the dosage form in a plurality of alignments between the delivery optics and the collection optics, and for each alignment, collecting probe light from said second surface, therefore allows a range of different scattering geometries through, and representative volumes of the dosage form to be tested. The analyser may then use the Raman spectral features from the various alignments in a number of ways, determining one or more properties of the dosage form using the Raman spectral features detected during some or all of the alignments.

For example, in one mode of operation the analyser may process the detected Raman spectral features for each alignment or each of a plurality of groups or ranges of alignment to derive a separate dosage form property for each such alignment, group, or range, and then average or combine the obtained dosage form properties to obtain a single average dosage form property which is more representative of the whole dosage form.

In another mode of operation, the analyser may instead average or otherwise combine together the Raman spectral features from each alignment or each of a plurality of groups or ranges of alignment, to determine a more representative set of Raman spectral features for the whole dosage form, from which a more representative dosage form property for the whole dosage form can be derived.

In other modes of operation, a separate value of a property of the dosage form may be determined for each of a plurality of different alignments, or group or range of alignments, for example so as to determine a separate value of a property of the dosage form for each of two or more different parts of the dosage form. For example, such modes of operation may for example be used to detect a separate value for each of two or more frangibly separable parts of a pharmaceutical tablet, typically defined by one or more break lines 14 or grooves in one or more faces of the tablet, such as the debossed snap line feature seen in FIG. 3b.

Multiple alignments of a dosage form at the test location can be achieved more readily using the described arrangements because of the use of Raman spectroscopy which permits the dosage form to be held at the test location without requiring light baffles or other arrangements to strongly prevent probe light from passing around the dosage form to the probe light collection optics. This is in contrast to the use of infrared absorption spectroscopy where leakage of probe light around the dosage form is of much more concern, making that type of optical testing of the dosage form over a range of alignments (translations and/or rotations) much more difficult because the dosage form will usually need to be held in some kind of light tight surround. To this end, and as discussed elsewhere, the gripper used in the present embodiments may be arranged to suspend the dosage form in essentially free space between the delivery optics and collection optics of the Raman analysis station, without any baffles or other particular light blocking structures being needed.

Referring back to FIG. 7, the mechanical gripper (represented by cross sections through opposing jaws 94) is controlled to translate the dosage form 12 laterally between the delivery and collection optics, so that the first surface region 710 translates across an upper surface 40 of the dosage form 12, and at the same time the second surface region 712 translates across a lower surface 41 of the dosage from. The dosage form may be held stationary in each of two or more particular such alignments, and Raman spectral features detected for each such discrete alignment, and/or Raman spectral features may be detected during one or more episodes of continuous movement of the dosage form 12.

The depicted lateral translation allows a larger volume of the dosage form to be sampled, while retaining use of a probe light beam 27 (and therefore first surface region 710) of modest diameter which may be easier to provide in an optically consistent manner, and using a second surface region of modest diameter which can also improve consistency of light collection. In order to improve consistency of probe light delivery and collection it may be preferable to use optics with fixed probe light spot size on the dosage form 12, and a fixed collection spot size, and to avoid telescope or other moving optics arrangements. For example, a desirable first surface region 710 or delivery light spot size may be less than about 3 mm, or less than about 2 mm in diameter.

Although an essentially lateral translation is depicted in FIG. 7 between two or more positions, these positions could be distributed in various ways, for example in a straight line across the dosage form, in a spiral form, using a two dimensional array of evenly spaced sampling points and so forth. Although the translation in FIG. 7 is depicted as being lateral, some vertical movement (towards/away from the delivery optics/collection optics) may also be desirable, for example to ensure that the second surface region is maintained at a substantially constant distance from the collection optics. This may particularly be desirable to maintain the second surface region at a suitable focal distance from the collection optics so as to maintain constant light collection characteristics.

Figure 8:
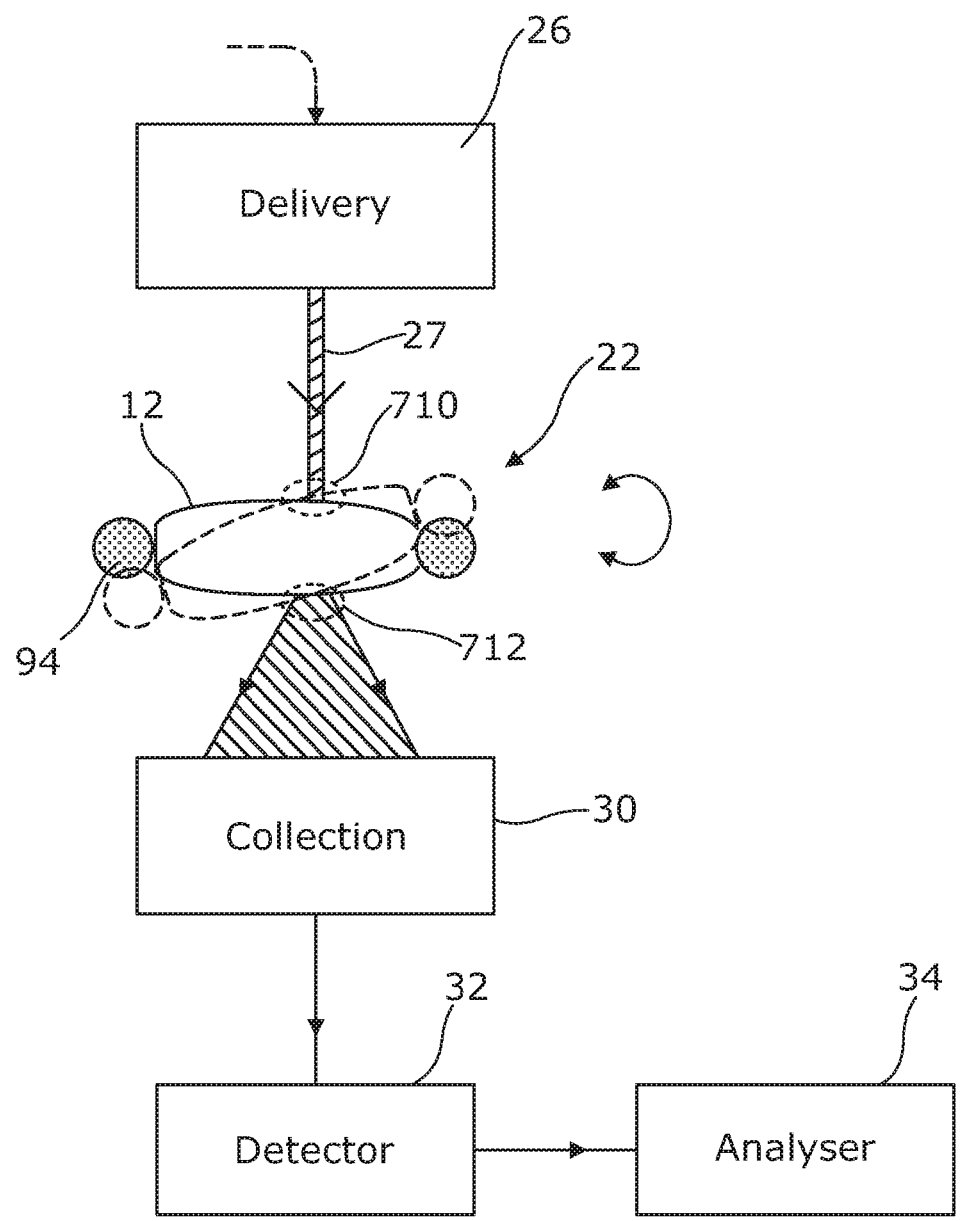

In FIG. 8 the gripper is seen to be controlled to rotate the dosage form 12 about one or more axes, which could be perpendicular to the optical axes of the delivery and collection optics as depicted in FIG. 8, or could be or include other axes. As for FIG. 7, the dosage form may be held stationary in each of two or more particular such alignments, and Raman spectral features detected for each such discrete alignment, and/or Raman spectral features may be detected during one or more episodes of continuous movement of the dosage form 12. In FIG. 7 the degree of rotation depicted in around thirty degrees, but a range of alignments over a much smaller range of angles may be used, or over a larger range of angles. In some embodiments, the dosage form may be completely inverted or turned over between alignments, so that one or more alignments involve probe light scattering through the sample in one direction, and one or more alignments involve the probe light scattering through the sample in the other direction.

One or more such rotational movements may be combined with one or more translational movements (for example as depicted in FIG. 7) to provide a number of different alignments, in each of which at least one of the position of the first surface region on the dosage form and the position of the second surface region on the dosage form is different, thereby providing a different optical path for scattering of the probe light through the sample for analysis as discussed above.

If translation is used then the range of translation of the dosage form involved in providing the plurality of alignments may typically be of the order of a few mm, for example at least 2 mm. If rotation is used then the range of rotation of the dosage form involved in providing the plurality of alignments may vary widely, for example being at least a few degrees or at least 10 degrees. One or more full inversions of the dosage form may involve a range of rotation of about 180 or about 360 degrees.

Figure 9:
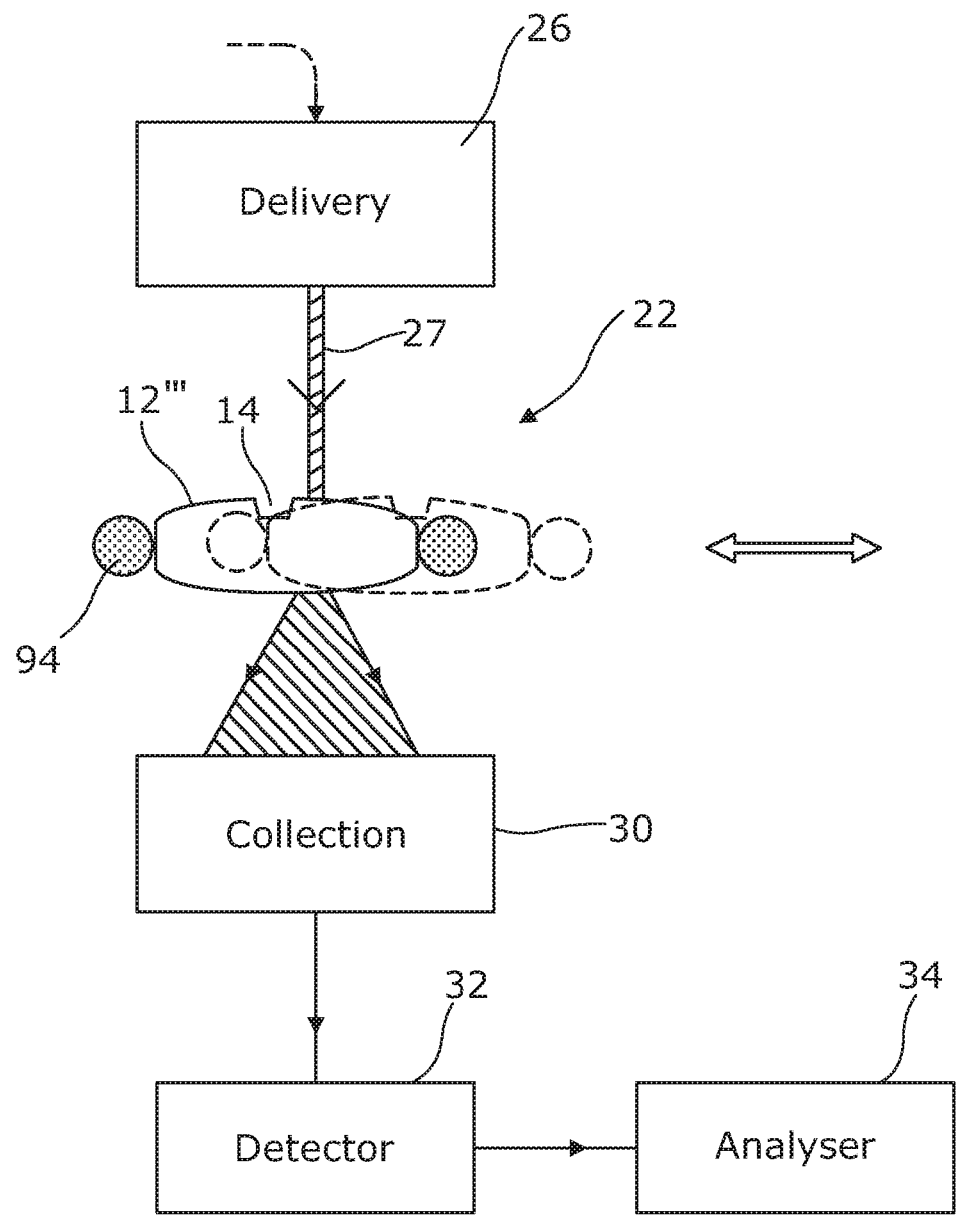
FIG. 9 shows how the value of a property for each of two sub-dose portions of a single dosage form, typically separated by a surface groove or other break line, may be determined.

FIG. 9 is similar to FIGS. 7 and 8 but depicts the translation of a dosage form 12''' similar to that of FIG. 3b in which a break line 14 or debossed snap line feature is provided across a surface of the dosage form to facilitate breaking the dosage form into two parts, such as two half doses. In this case, one or more alignments in which Raman spectral features are measured provide for first and second surface regions in one half dose, and one or more alignments in which Raman spectral features are measured provide for first and second surface regions in the other half dose. In this way, one or more properties of the dosage form can be separately determined for each half dose. Of course, some dosage forms may be similarly structured for breaking into three or more separate doses, and one or more alignments corresponding to each such dose may be used to determine one or more properties for each such dose.

Figure 10:
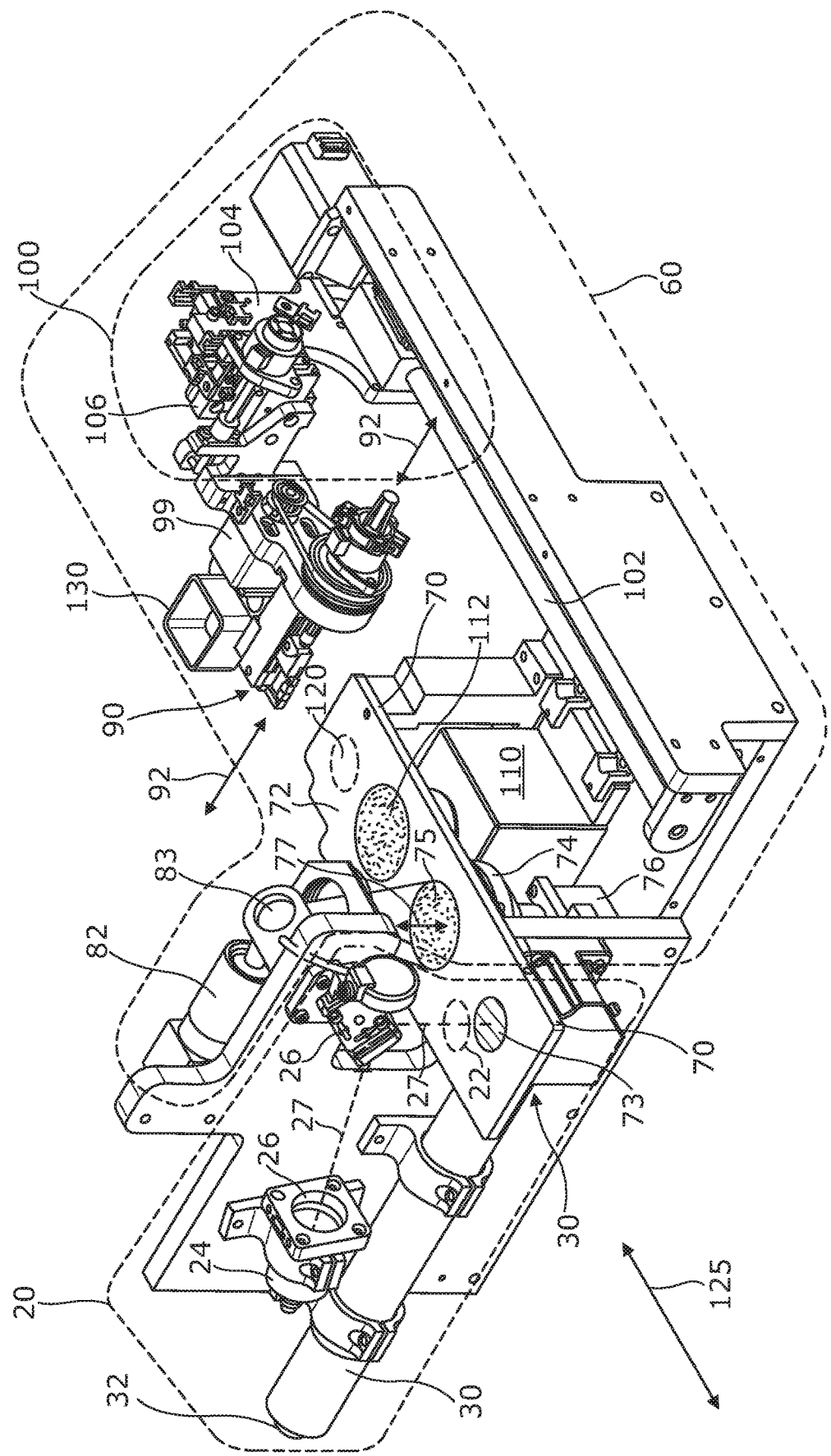
FIG. 10 shows some engineering details of how apparatus of FIGS. 1 and 2 may be implemented.

FIG. 10 provides in perspective view a detailed drawing of apparatus implementing the dosage handler 60 and some other aspects illustrated in FIGS. 1 and 2. For clarity and convenience however, FIG. 10 does explicitly show any of the dosage source 42, the controller 50, the analyser 34, or the personal computer 36 seen in the earlier figures.

The dosage handler is generally depicted within the dashed balloon labelled 60. The multi-axis staging depicted generally within the dashed balloon 100 provides movement of the gripper 90 and box slider 130 as required to implement the handling processes described above in relation to the handling table 70. The horizontal table surface 72 of the handling table 70 comprises the drop zone 120 where the dosage source (not shown) drops a dosage form into the box slider 130, the weighing scale surface 112 of weighing scale 110 to which the box slider 130 moves the dosage form for weighing, and the rotation stage surface 75 of rotation stage 74, to which the box slider 130 moves the dosage form after weighing. The rotation stage 74 is driven by the rotation stage motor 76.

The machine vision system includes the machine vision camera 82 which has a field of view covering some or all of the rotation stage surface 75 by virtue of machine vision mirror 83, so that the machine vision system can detect at least an alignment of a dosage form lying in the plane of the handling table surface such that the dosage form can be aligned to a preferred alignment by rotation of the rotation table. The machine vision system preferably also detects further orientation information of the dosage form so that it can be rotated by the gripper 90 about the gripper rotation axis 92 to a desired orientation of rotation, the gripper axis being parallel to the table surface 72. In FIG. 10 rotation of the gripper is driven by a gripper rotation motor 99 through a belt drive.

The Raman analysis station is generally depicted within dashed balloon 20, and comprises a laser source 24 to generate a probe beam 27 of laser light, delivery optics 26, collection optics 30, and detector 32. The test location 22 in FIG. 10 is located close above the handling table 70. The drop zone 120, weighing scale surface 112, and rotation stage surface 75 are generally distributed along a process axis 125, and the test location 22 is conveniently located along the same axis beyond the rotation stage surface 75. The probe beam 27 of laser light is directed downwards by delivery optics 26 towards the test location 22 which is above an aperture 73 through the handling table 70. A dosage form is held by the gripper 90 for optical analysis at the test location above the aperture 73, and the collection optics 70 which are partly located beneath the handling table receive the probe light scattered within the held dosage form through the aperture 73, to thereby achieve a transmission configuration for optical analysis.

The multi-axis staging 100 is arranged to run along a rail 102 which is parallel to the process axis 125 so as to provide the required access by the box slider 130 to the drop zone 120, weighing scale surface 112 and rotation stage surface 75, and the required access by the gripper 90 to the rotation stage surface 75 and the test location 22. Vertical motion of the gripper 90 and box slider 130 is provided by a common vertical axis mechanism of the multi-axis staging 100, and depth motion across the table surface perpendicular to the process axis 125 is provided by a common depth axis mechanism of the multi-axis staging.

While particular embodiments of the invention have been described with reference to the drawings, the skilled person will be aware of various modifications and changes can be made to these embodiments without departing from the scope of the invention.

The invention claimed is:

1. A method of automatic analysis of a pharmaceutical dosage form, comprising:
   grasping the dosage form using a gripper;
   moving the gripper so as to bring the dosage form to a test location between delivery optics arranged to direct probe light to a first surface region of the dosage form, and collection optics arranged to receive probe from a second surface region of the dosage form following scattering through said dosage form;
   moving the gripper to present the dosage form in a plurality of alignments between the delivery optics and the collection optics, and for each alignment, collecting probe light from said second surface;
   detecting Raman spectral features of received probe light for each of the plurality of alignments;
   determining a property of the dosage form using the Raman spectral features detected during some or all of the alignments;
   wherein a different value of the property is determined for each of two or more parts of the dosage form, using Raman spectral features collected during one or more alignments where the first and second surface regions are found on each such part of the dosage form.

2. The method of claim 1 wherein the property is an average property for the dosage form determined using Raman spectral features detected during all of the alignments.

3. The method of claim 1 wherein the two or more parts of the tablet are defined by break lines provided on a surface of the tablet.

4. The method of claim 1 wherein at least one of the position of the first surface region on the dosage form and the position of the second surface region on the dosage form changes between each alignment.

5. The method of claim 1 wherein between each alignment the gripper moves the dosage form through one or both of a translation and a rotation.

6. The method of claim 1 wherein at least some of the alignments form one or more continuous ranges of alignments during movement of the dosage form, in which the Raman spectral features are detected in the received probe light.

7. The method of claim 1 wherein the second surface region is on an opposite side of the dosage form from the first surface region.

8. The method of claim 1 wherein the pharmaceutical dosage form is one or more of: a tablet; a coated tablet; a capsule; a gelcap; a solid dosage form; and an oral dosage form.

9. The method of claim 1 wherein movement of the dosage form to provide the plurality of alignments includes at least one of:
   translation of the dosage form over a distance of at least 2 mm; and rotation of the dosage form through at least 10 degrees.

10. Apparatus for automatic analysis of a pharmaceutical dosage form, comprising:
    a mechanical gripper arranged to grasp the dosage form;
    a Raman analysis station having a test location and arranged to detect Raman spectral features in probe light scattered within the dosage form when positioned at the test location;

a controller arranged to control the gripper so as to present the dosage form in a plurality of alignments within the test location, and to control the Raman analysis station to collect probe light scattered within the dosage form and detect Raman spectral features in the collected probe light, in each of the alignments; and an analyzer arranged to determine one or more properties of the dosage form from the detected Raman spectral features;

wherein the apparatus is arranged to determine a different value of one of the properties for each of two or more parts of the dosage form, using one or more alignments in which the probe light scatters predominantly through each such part of the dosage form.

11. The apparatus of claim 10 wherein the Raman analysis station comprises delivery optics arranged to direct probe light to a first surface region of the dosage form, and collection optics arranged to receive probe from a second surface region of the dosage form following forward scattering through said dosage form, when the dosage form is presented within the test location.

12. The apparatus of claim 11 wherein at least one of the position of the first surface region on the dosage form and the position of the second surface region on the dosage form moves between subsequent alignments.

13. The apparatus of claim 10 wherein the controller is arranged to control the gripper so as to rotate and/or translate the dosage form between each alignment.

14. The apparatus of claim 10 wherein at least some of the alignments form one or more continuous ranges of alignments during movement of the dosage form in which the Raman spectral features are detected in the received probe light and used for determining one or more properties of the dosage form.

15. The apparatus of claim 10 wherein at least one of the one or more determined properties is an average property for the dosage form determined using the detected Raman spectral features from all of the alignments.

16. The apparatus of claim 10 arranged to determine a different value of one of the properties for each of two or more parts of the dosage form, using one or more alignments in which the probe light scatters predominantly through each such part of the dosage form.

17. Apparatus for analysing a pharmaceutical dosage form, comprising:
a rotation stage having a rotation stage surface arranged to receive a dosage form;
a gripper arranged to grasp the dosage form;
a Raman analysis station having a test location and arranged to detect Raman spectral features in probe light scattered within the dosage form when positioned at the test location; and
a controller arranged to control rotation of the rotation stage so as to rotate the dosage form when on the stage surface to a preferred alignment, to control the gripper to grasp the dosage form in the preferred alignment, and to control the gripper to carry the grasped dosage form to the test location for Raman analysis.

18. The apparatus of claim 17 wherein the Raman analysis station comprises:
delivery optics arranged to direct probe light to a first surface region of the dosage form when located at the test location;
collection optics arranged to receive said scattered probe light from a second surface region of the dosage form, the second surface region being spaced from the first surface region; and
a detector arranged to detect the Raman spectral features in the received probe light.

* * * * *